United States Patent
Weidmann

(10) Patent No.: US 9,366,622 B2
(45) Date of Patent: Jun. 14, 2016

(54) HETERODYNE DETECTION SYSTEM AND METHOD

(71) Applicant: Damien Weidmann, Reading (GB)

(72) Inventor: Damien Weidmann, Reading (GB)

(73) Assignee: ITI SCOTLAND LIMITED, Glasgow (GB)

(*) Notice: Subject to any disclaimer, the term of this patent is extended or adjusted under 35 U.S.C. 154(b) by 0 days.

(21) Appl. No.: 14/380,685

(22) PCT Filed: Feb. 22, 2013

(86) PCT No.: PCT/GB2013/050448
§ 371 (c)(1),
(2) Date: Aug. 22, 2014

(87) PCT Pub. No.: WO2013/124678
PCT Pub. Date: Aug. 29, 2013

(65) Prior Publication Data
US 2015/0014543 A1   Jan. 15, 2015

(30) Foreign Application Priority Data
Feb. 22, 2012 (GB) .................................. 1203042.5

(51) Int. Cl.
*G01N 21/49* (2006.01)
*G01S 17/32* (2006.01)
(Continued)

(52) U.S. Cl.
CPC ............... *G01N 21/49* (2013.01); *B82Y 20/00* (2013.01); *G01N 33/0027* (2013.01);
(Continued)

(58) Field of Classification Search
CPC .................... G01N 21/49; G01N 2201/06113; G01N 2201/0636; G01N 33/00; G01N 21/39; G01N 21/3581

USPC .......................................................... 250/349
See application file for complete search history.

(56) References Cited

U.S. PATENT DOCUMENTS 4,325,635 A * 4/1982 Sattler et al. .................. 356/484
5,751,830 A * 5/1998 Hutchinson .................. 382/103
(Continued)

FOREIGN PATENT DOCUMENTS

WO   WO-2007050134 A2   5/2007
WO   WO-2010108705 A1   9/2010
WO   WO-2011058330 A1   5/2011

OTHER PUBLICATIONS

Mikaelian, T. et al., "A high-speed retro-reflector for free-space communication based on electro-optic phase modulation", Aerospace Conference Proceedings, 2002, IEEE Mar. 9-16, 2002, Piscataway, NJ, USA, IEEE, vol. 3, Mar. 9, 2002, pp. 1487-1492, XP01604283, ISBN: 978-0-7803-7231-3.

(Continued)

*Primary Examiner* — Marcus Taningco
(74) *Attorney, Agent, or Firm* — Perkins Coie LLP

(57) ABSTRACT

An active heterodyne detection system comprises a continuously tuneable laser source (1) emitting infra-red radiation, means (8) to split the infra-red radiation into a first part and a second part, means (4) to provide a frequency shift between the first part and the second part, means (8, 9) to direct the first part of the infra-red radiation to a target (2), means (4) to provide the second part of the infra-red radiation as a local oscillator, means (8, 9) to collect a scattered component of the first part of the infra-red light from the target (2), and means (5) to mix the scattered component and the local oscillator and route them to a detector (3) for heterodyne detection over a continuous spectral range. A method of active heterodyne detection over a continuous spectral range is also disclosed.

20 Claims, 10 Drawing Sheets

(51) Int. Cl.
- *G01S 17/95* (2006.01)
- *G01S 7/491* (2006.01)
- *B82Y 20/00* (2011.01)
- *G01N 33/00* (2006.01)
- *H01S 5/022* (2006.01)
- *H01S 5/34* (2006.01)
- *H01S 5/024* (2006.01)

(52) U.S. Cl.
CPC .............. *G01S 7/4911* (2013.01); *G01S 17/32* (2013.01); *G01S 17/95* (2013.01); *G01N 2201/066* (2013.01); *G01N 2201/0636* (2013.01); *G01N 2201/06113* (2013.01); *H01L 2924/0002* (2013.01); *H01S 5/02264* (2013.01); *H01S 5/02415* (2013.01); *H01S 5/02469* (2013.01); *H01S 5/3401* (2013.01)

(56) References Cited

U.S. PATENT DOCUMENTS 7,986,397 B1  7/2011  Tiemann et al.
2010/0029026 A1  2/2010  Berger et al.
2010/0067554 A1*  3/2010  Wysocki et al. ............... 372/20

OTHER PUBLICATIONS

Mariano, Troccoli et al., "High-Peformance Quantum Cascade Lasers Grown by Metal-Organic Vapor Phase Epitaxy and Their Applications to Trace Gas Sensing", Journal of Lightwave Technology, IEEE Service Center, New York, NY, vol. 26, No. 21, Nov. 1, 2008, pp. 3534-3555, XP011241670, ISSN: 0733-8724, DOI: 10.1109/JLT.2008.925056.

Tsai, T. et al., "Fast wavelength tuning of external cavity quantum cascade lasers", Lasers and Electro-Optics, 2009 and 2009 Conference on Quantum Electronics and Laser Science Conference, CLEO/QELS 2009, Conference on, IEEE, Piscataway, NJ, Jun. 2, 2009, pp. 1-2, XP(31520878, ISBN: 978-1-55752-869-8.

International Search Report and Written Opinion PCT/GB2013/050448 dated Jul. 28, 2013, pp. 1-18.

Search Report for Application No. GB1203042.5 dated Jun. 21, 2012, 1 page.

* cited by examiner

Extended surface

Aerosol target

Bistatic

Monostatic

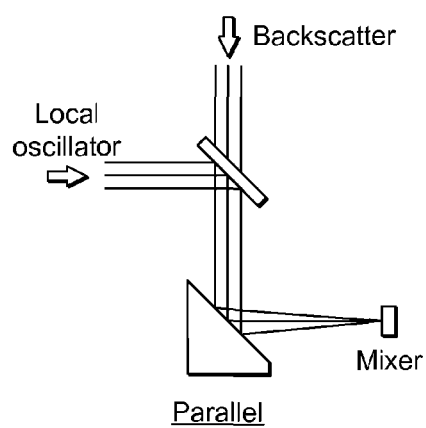
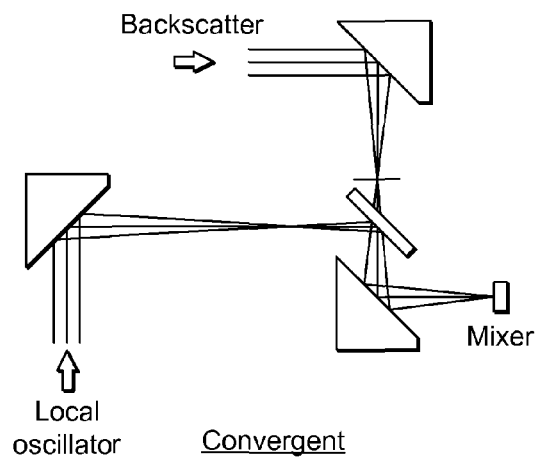
FIG. 7(a)  FIG. 7(b)
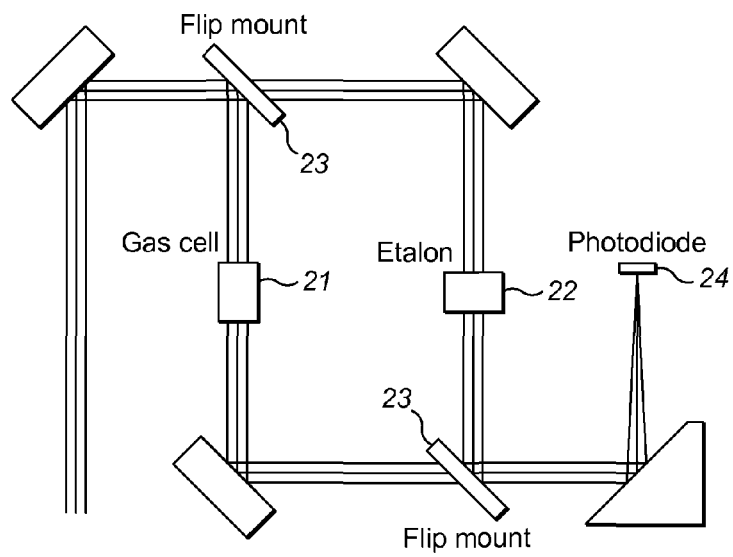
FIG. 8

HETERODYNE DETECTION SYSTEM AND METHOD

CROSS-REFERENCE TO RELATED APPLICATIONS

This application is a 35 USC §371 application of International Application No. PCT/GB2013/050448 filed Feb. 22, 2013, which claims priority to Great Britain patent application no. GB 1203042.5 filed Feb. 22, 2012, both of which are hereby incorporated by reference in their entirety.

FIELD OF INVENTION

The present invention relates to a heterodyne detection system and a method of using heterodyne detection. In particular embodiments, the invention provides for detection of signals in the infrared, particularly the medium and long wavelength infrared, suitable for determining vibrational and rotational spectra of molecules present in small concentration to allow remote detection of such molecules.

BACKGROUND OF INVENTION

A number of techniques are currently available for detection and measurement of airborne or atmospheric constituents using information from their ro-vibrational spectra. The spectral absorption lines of interest for small molecules that form such constituents are typically in the infrared region. Such techniques may be passive, in that the light originates from an incoherent source such as the sun, or active, in which light from a light source is used to illuminate a target and backscattered light is sensed by an associated detector.

The most generally used active technique is LIDAR (light detection and ranging), which involves using a laser to illuminate the target with coherent radiation for either direct or heterodyne detection of backscattered radiation. Such techniques are used commercially and are widely described in the academic literature, for example in "Laser Remote Sensing (Optical Science and Engineering), Tetsuo Fukuchi (Editor) CRC Press (28 Jun. 2005); and "Elastic Lidar", V. A. Kovalev and W. E. Eichinger, Wiley-Interscience 2004. LIDAR systems are extensively used in atmospheric measurement, particularly by NASA. $CO_2$ gas lasers provide acceptable levels of power in spectral ranges of interest and have been extensively used as the illumination source. Either a continuous or a pulsed laser may be used, though each has been found to have advantages and disadvantages. Continuous systems have generally not been effective for vapour phase targets, but have advantages for heterodyne detection, whereas pulsed systems have been effective for direct detection of vapour phases.

Heterodyne detection techniques involve the use of a local oscillator whose signal is combined with detected light to allow significantly greater sensitivity than is available through direct detection. In effect, beats between the local oscillator and the detected light are used to amplify the signal of interest, which can then be reconstructed by appropriate calculation. The local oscillator may be obtained in a continuous LIDAR system by splitting the light (for convenience, the term "light" will be used hereafter for all such systems, although the techniques used may be employed across a wide range of the electromagnetic spectrum) from the laser source to form two beams. While part of the light is used to illuminate the target and so provide the signal to be evaluated, another part of the light is shifted in frequency by a component such as an acousto-optical modulator (AOM) to serve as the local oscillator and subsequently combined with the backscattered signal for detection. In pulsed LIDAR heterodyne systems, this approach has not been effective and a separate local oscillator has been used which needs to be frequency stabilized to ensure frequency overlap with the backscattered radiation from the target. The pulse profile of existing pulsed laser systems can also affect temporal resolution and make relatively short range measurements difficult to achieve.

Active heterodyne detection systems using $CO_2$ gas lasers have been used for atmospheric sensing of target molecules over significant ranges, but these systems still have significant challenges, particularly for use with gaseous targets. As can be seen from FIGS. 2a and 2b, back scattering from a solid target is much greater than back scattering from an aerosol target, because a scattering event may be over a widely distributed scattering space rather than predominantly backscattered broadly towards the source. A particularly effective LIDAR technique for detection is Differential Absorption LIDAR (DIAL), which involves taking measurements on and off resonance with the target gas species absorption and measuring the differential absorption between the two. This principle is shown in FIGS. 3a and 3b. FIG. 3a illustrates the difference in signal between on resonance and off resonance, and as is shown with FIG. 3b, the differential in received power is effective for distance measurement. Although this approach has the potential for great sensitivity, it requires very accurate control of the laser lines used. Use of $CO_2$ gas lasers is also problematic when high sensitivity is required, as results are affected by absorption from atmospheric $CO_2$.

US 2010/0029026 is directed to a method of constructing a mid- or far-IR device on a chip for analysing a scene. The device comprises a QCL and a QCD (Quantum Cascade Detector), preferably epitaxially grown together on the same substrate. It is suggested that the device could be constructed to allow heterodyne detection by splitting the QCL beam to use part as a local oscillator. The QCL laser and QCD detectors are constructed (using DFB techniques) each to operate at specific frequencies. To cover multiple frequencies, it is suggested to use a matrix of QCL lasers and detectors, each pair been optimised for a different frequency. In this arrangement, each laser source is carefully fixed in frequency, with pulsing techniques used to access a fixed frequency range to enable detection of a single vibration.

It is therefore desirable to produce a heterodyne detection system suitable for use to detect remote detection of target molecules over a wide range and with great sensitivity. Such a system would have particular benefits, for example in the remote detection of vapour traces from objects which it would be difficult or unsafe to inspect directly—this allows for remote inspection for gas leaks or for remote detection of explosive materials.

SUMMARY OF INVENTION

Accordingly, the invention provides an active heterodyne detection system comprising a continuously tuneable laser source emitting infra-red radiation, means to split the infra-red radiation into a first part and a second part, means to provide a frequency shift between the first part and the second part, means to direct the first part of the infra-red radiation to a target, means to provide the second part of the infra-red radiation as a local oscillator, means to collect a scattered component of the first part of the infra-red light from the target, and means to mix the scattered component and the local oscillator and route them to a detector for heterodyne detection over a continuous spectral range.

This approach provides a significant improvement upon conventional methods such as DIAL. Rather than restriction to one or a limited set of excitation wavelengths, it allows for the use of powerful heterodyne detection techniques over an extended range to provide hyperspectral detection. This approach can therefore be used to detect, in a single scan, a variety of different materials.

Advantageously, the continuously tuneable laser source is a quantum cascade laser. Other continuously tuneable sources such as OPOs and DFGs may also be used. OPOs and DFGs are considered to be laser sources in the context of the present application—that is, a broad rather than restrictive interpretation of the term laser source is employed.

Advantageously, temperature control means and current control means are provided to tune the wavelength and stabilize the frequency of the infra-red light.

Preferably, the laser source is provided in an external cavity configuration with a diffraction grating for wavelength selection and tuning.

In a preferred embodiment, the frequency shifting means is an acousto-optical modulator. The zeroth order mode of the acousto-optical modulator may then be used for monitoring of the laser source In one arrangement, the frequency shift is applied to the second part of the infra-red radiation and a first order mode of the acousto-optical modulator is used as the local oscillator. In another arrangement, the frequency shift is applied to the first part of the infra-red radiation and a first order mode of the acousto-optical modulator is directed to the target.

In one embodiment, monitoring of the laser source power is used to control an attenuator between the laser source and the acousto-optical modulator. This attenuator may be a polarizer. The polarizer may be mounted on a high-speed rotation stage, and the control may be by means of a PID (proportional-integral-derivative) system.

The laser source may be mounted on a cold plate cooled by a Peltier cooler, with the Peltier cooler is suspended from the cold plate. This is found to be particularly effective in achieving good signal quality by decoupling the laser source from any motion of the Peltier cooler, while allowing for effective Peltier cooling to stabilize temperature. The Peltier cooler may comprise a heat exchanger.

Advantageously, a mount for the continuously tuneable laser source may be provided with a support with high insulation and low thermal expansion. The support may comprise one or more fibreglass clamps. A plurality of ceramic elements may be provided on the one or more fibreglass clamps to support the mount at a plurality of point contacts.

The means to direct, collect and mix preferably comprises a reflective optical system. This may comprise one or more beam splitters.

In a further aspect, the invention provides a method of active heterodyne detection comprising: tuning a laser source to emit infra-red radiation to scan a continuous spectral range; splitting the infra-red radiation into a first part and a second part; providing a frequency shift between the first part and the second part; directing the first part of the infra-red radiation to a target; providing the second part of the infra-red radiation as a local oscillator; collecting a scattered component of the first part of the infra-red light from the target; mixing the scattered component and the local oscillator and routing them to a detector for heterodyne detection; and processing a detected signal to provide output over a continuous spectral range.

Advantageously, tuning the laser source comprises providing a sawtooth waveform to modulate an injection current of the laser source. The processing step may comprises use of an optimum estimation method to provide output.

BRIEF DESCRIPTION OF DRAWINGS

Specific embodiments of the invention will be described below, by way of example, with reference to the accompanying drawings, of which:

FIGS. 7a and 7b show alternative designs for use in beam mixing for heterodyne detection according to embodiments of the invention;

FIG. 8 shows an optical layout for local oscillator frequency calibration for use with embodiments of the invention;

DETAILED DESCRIPTION OF SPECIFIC EMBODIMENTS

Figure 1:
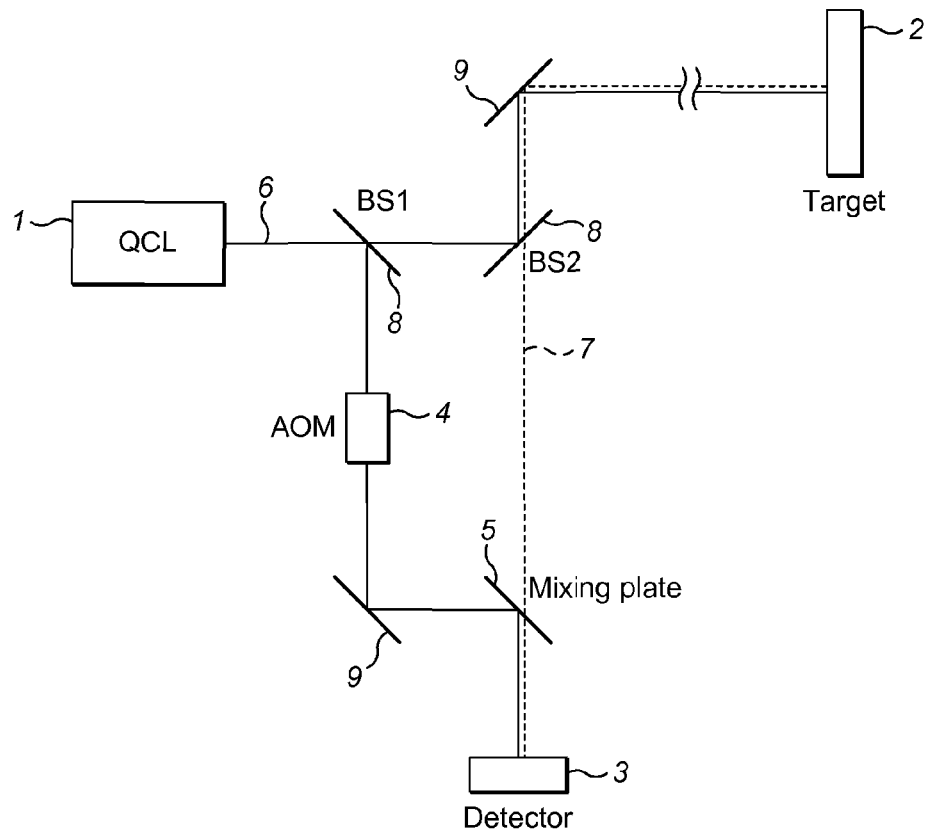
FIG. 1 shows schematically an active heterodyne detection system according to embodiments of the invention.
Figures 2A, 2B:
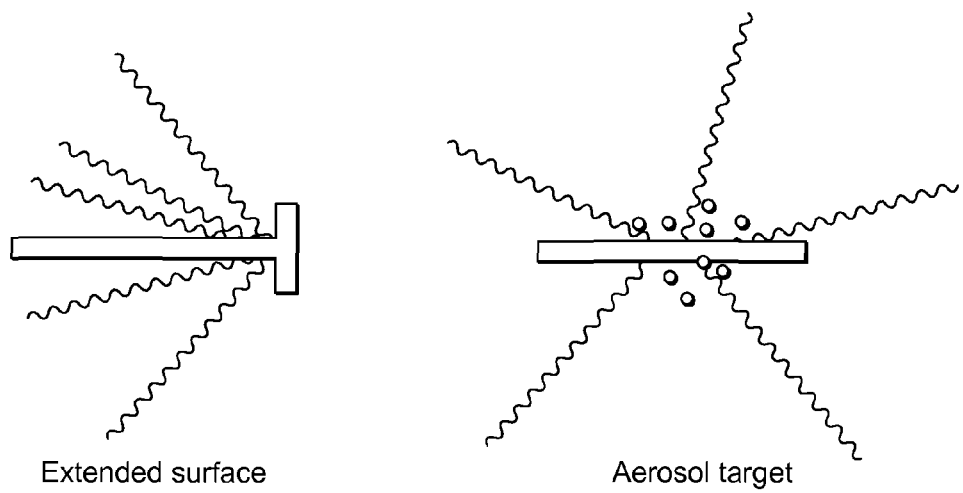
FIG. 2 shows a comparison between scattering from (a) an extended surface and (b) an aerosol target.

The basic elements of an active heterodyne detection system according to embodiments of the invention are shown in FIG. 1.

A continuously tuneable laser source 1 emits infra-red radiation. There are several such sources available, including optical parametric oscillators (OPOs), difference frequency generation devices (DFGs), but a preferred choice is to use a quantum cascade laser with an external cavity. Quantum cascade lasers (QCLs) with an external cavity are continuously tuneable laser sources well developed in the spectral region of 4 to 20 μm. Commercially available QCLs operate in continuous wave mode close to room temperature with output power up to 50 mW. Mid-infrared QCLs are now widely available from both large international suppliers and much smaller enterprises.

The emitted infra-red radiation 6 is used for two different purposes. Means are provided to split this radiation into a first and second part—in this case, the means is provided by a first beam splitter 8. A first part of this radiation is directed by an optical system (in this case comprising a further beam splitter 8 and a mirror 9) to a remote target 2. A second part of this radiation is not routed to the target at all.

This second part of the radiation is routed to a means to shift a frequency of the second part of the infra-red radiation—in this case, the frequency shifting means is an acousto-optical modulator 4. This provides the local oscillator for the active heterodyne detection system.

Scattering takes place at the target 2, and the system also comprises means to collect a scattered component (in practice, a backscattered component) of the first part of the infra-red light from the target 2. This received light 7 passes through the mirror 9 and beam splitter 8b as before, but it takes a different path through the beam splitter 8b and passes through to a mixing plate 5.

Mixing plate 5 is a means to mix the scattered component received from the target and the frequency-shifted second part of the infra-red radiation together to provide a signal for heterodyne detection. This mixed signal is routed to a detector 3 with appropriate associated computing capability for heterodyne detection and subsequent computation and analysis.

The overall theoretical approach will now be briefly described. The skilled person will appreciate that more detail is provided in the references indicated below and in the literature of lidar, DIAL, and heterodyne detection. Analysis related to lidar and DIAL may be applied without difficulty to arrangements which involve a continuously tuneable laser source with observation over a continuous spectral range—as the person skilled in the art will appreciate, while the need to consider a range of source wavelengths and a range of detection wavelengths may increase the complexity of signal processing, it does not fundamentally change the analysis.

Lidar operates by the backscattering of laser power into a detector from a remote object which may include aerosols or extended surfaces. The basic operation of lidar is described by Equations 1 to 5 below:

The Lidar equation $$P(R, \lambda) = E(\lambda)G(R)\beta(R, \lambda)T(R, \lambda) \quad \text{Equation 1}$$

$$E(\lambda) = P_T(\lambda)KA \quad \text{Equation 2}$$

$$G(R) = \frac{O(R)}{R^2} \quad \text{Equation 3}$$

$$\beta(\lambda, R) = \overline{N(R)}\frac{d\sigma(\lambda, \pi)}{d\Omega} \quad \text{Equation 4}$$

The lidar equation (Equation 1) relates the amount of power backscattered onto the detector $P(R, \lambda)$ to various parameters including the specific geometry of the instrument and the composition of the atmosphere. This equation is only valid for distances much greater than the receiver aperture. $E(\lambda)$ is a system parameter which includes the transmitted power $P_T(\lambda)$ and the collection efficiency K and area A of the receiving optics (Equation 2). Equation 2 is applicable to both pulsed and continuous lasers. The geometric factor $G(R)$ (Equation 3) includes the overlap between the transmitted beam and the receiver field of view $O(R)$ and a quadratic dependence on the distance R between the transmitter and the target (i.e. light is uniformly scattered onto a sphere of radius R).

The terms $\beta(R,\lambda)$ and $T(R,\lambda)$ in Equation 2 relate to the properties of the target (either surface or aerosol) and to the atmosphere. The backscatter term $\beta(R,\lambda)$ includes terms for the backscattering; for extended surfaces this is simply the diffuse reflectance of the target. Since backscattering by extended surfaces is generally much greater than for aerosol targets, only the scattering from the extended surface is considered in this specific case. For scattering by atmospheric aerosols alone (Mie scattering), the backscattering coefficient is a sum (or an integral) over the whole transmitted beam path of the product of the number density of a particular particle type and the scattering constant for that particular particle type (Equation 4 where $N(R)$ is the average particle concentration at distance R, and $d\sigma/d\Omega$ the backscattering cross-section per unit solid angle). Given a particular distribution of particles it is possible to calculate the backscattering term. In the infrared spectral region, it is assumed that Mie scattering (i.e. particulate scattering) dominates over molecular scattering (Rayleigh scattering).

The atmospheric extinction term $T(R,\lambda)$ is a measure of the transmission of the atmosphere at a particular wavelength (Equation 5 where $\alpha(R,\lambda)$ is the extinction coefficient) where the integral extends across the whole beam path. The extinction coefficient includes the influence of all species present along the atmospheric path and is a sum of the absorption by molecules and the scattering/absorption of aerosols and particles (Rayleigh scattering by molecules in the infrared can be neglected). For an atmosphere with no variation in extinction coefficient over the beam path (i.e. $\alpha(R,\lambda)=\alpha(\lambda)$), the term in the integral reduces to $\alpha(\lambda).R$; more complex atmospheric compositions (i.e. smoke plumes, cloud layers, etc.) can be considered if the dependence of the extinction coefficient on distance is known.

When scattering from aerosols is considered, the following approach is used (using an analysis derived from B. N. Whiteside and R. M. Schotland, "Development of a 9.3 μm CW lidar for the study of atmospheric aerosol", Final technical report NASA NAG8-766 N93-29105 1993). The laser is focused at a distance from the detector to a waist size $w_0$; the Rayleigh distance $Z_R$ (Equation 6) defines the distance over which the beam is approximately collimated. Beyond this volume the intensity of the beam drops rapidly as the beam size increases, resulting in less backscatter. Furthermore, the field-of-view restrictions inherent in heterodyne detection greatly reduce the detected signal from backscatter occurring beyond the volume. In effect, focusing the laser (and the ability to change the focal conditions) allows range-resolution with a continuous laser. Equation 7 gives the backscattered power at the detector, $P_T$ is the transmitted laser power (W), $\beta$ is the volume backscattering constant ($m^{-1}sr^1$), $Z_R$ is the Rayleigh length (m), $A_R$ is the area of the receiver ($m^2$), K is the collection efficiency of the optical system, R is the distance to the focal point (m) and $\alpha(\lambda)$ is the wavelength dependent atmospheric extinction coefficient ($m^{-1}$) at the wavelength of the laser. Equation 7 can be derived from Equation 1 if the system parameter (E) is defined by $P_T A_R K$, the geometric parameter $G(R)$ by $2Z_R/R^2$, the backscattering coefficient $\beta(R)$ by $\beta$ (i.e. scattering constant with distance) and the atmospheric attenuation $T(R)$ by $\exp(-2\alpha(\lambda)R)$ valid for the case of an homogenous atmosphere.

Rayleigh distance $$Z_R = \frac{\pi w_0^2}{\lambda} \quad \text{Equation 6}$$

Aerosol backscattered power $$P = \frac{2P_T \beta Z_R A_R K}{R^2}\exp(-2\alpha(\lambda)R) \quad \text{Equation 7}$$

$$P = 2P_T \beta K\lambda \exp(-2\alpha(\lambda)R) \quad \text{Equation 8}$$

Field of view for heterodyne detection $$FoV = \frac{4\lambda}{\pi D_R} \quad \text{Equation 9}$$

Equation 7 can be used to calculate the backscattered power at the receiver. However, the inherently restricted field of view of heterodyne detection systems (Equation 9—the field of view of a heterodyne detector (in radians) is given by Equation 9 where $D_R$ is the diameter of the receiving optics and $\lambda$ is the laser wavelength—this is inherently limited by the coherent nature of the detection process) means that only a fraction of the total backscattered radiation is actually detected (i.e. O(R)<1). The impact of this is that the waist of the beam should be matched to the field of view at all distances with a corresponding influence on the Rayleigh length (Equation 6). For a fixed size of receiver the field of view is constant and the spatial extent of the sampled area scales with distance. Hence, the waist size increases linearly with distance while the Rayleigh length scales with the square of the distance (Equation 6). This leads to the result that the detected backscattered power is approximately constant with distance (Equation 8) since the Rayleigh length and the distance term effectively cancel. Similarly, the dependence on receiver size $A_R$ is also removed; the diameter of the receiver only influences the Rayleigh length and hence the range resolution of the instrument. If the wavelength is chosen carefully, atmospheric attenuation (the exponential term in Equations 7 and 8) has only a minimal effect over relatively short distances (<100 m) with small extinction coefficients (ca. $10^{-4}$ m$^{-1}$).

The volume backscattering constant $\beta$ is the summation over all scattering particles. Under certain limiting assumptions (e.g. spherical particles with a defined size distribution) it is possible to calculate this parameter or to fit experimental data to a model. For a moderately clean atmosphere $\beta$ is of the order of $10^{-7}$ m$^{-1}$sr$^{-1}$ at ground level. Volcanic eruptions or industrial pollution can greatly increase this value over local or regional scales. The atmospheric extinction coefficient $\alpha(\lambda)$ is a measure of the transmission of the atmosphere and includes absorption by atmospheric gases (including continuum absorption) and attenuation (scattering and absorption) by aerosols.

From Equation 8, it is clear that (for a given wavelength) the power scattered back to the detector is proportional to the transmitted laser power $P_T$, the backscattering coefficient $\beta$ and the collection efficiency of the optical system K and displays a negative exponential dependence on the extinction properties of the atmosphere and the distance. Increasing the extinction coefficient by an order of magnitude has a dramatic effect on the amount of backscattered power at the detector. Detection of this difference that allows quantitative information on concentration of the species of interest to be obtained.

Backscattering from an extended surface is described theoretically in very similar terms to aerosol scattering; Equation 10 gives the backscattered power at the detector for an extended surface at distance R with a diffuse reflectivity of $\rho$. The other terms are identical to those defined in Equation 7. The surface reflectivity replaces the volume backscattering constant ($\rho/2\pi$ versus $2\beta Z_R$) with the result that scattering from an extended surface produces significantly more power at the detector for typical values of $\rho$ and $\beta$ (a reflectivity of ca. 0.01 to 0.1 compared to a volume backscattering coefficient of $10^{-7}$). Equation 10 assumes that the diameter of the laser radiation incident on the target is similar to (or smaller than) the field of view of the detector (i.e. O(R)=1). This is an entirely reasonable assumption in the case of heterodyne detection. An extended surface will provide much greater power than an aerosol target, but with the same dependence on extinction coefficient.

Extended surface backscattered power $$P = \frac{P_T \rho A_R K}{2\pi R^2} \exp(-2\alpha(\lambda)R) \quad \text{Equation 10}$$

Figure 3:
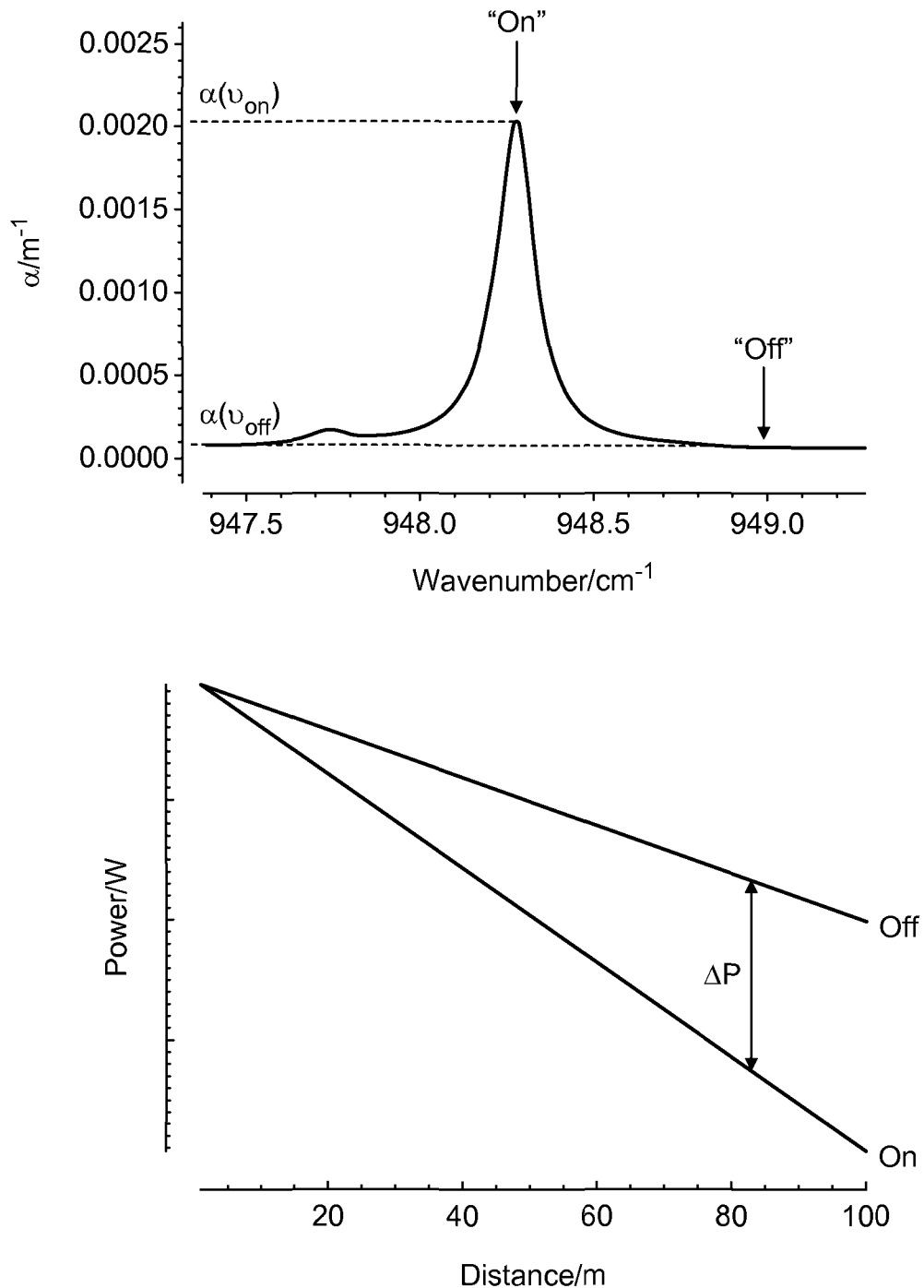
FIG. 3 illustrates the operation of differential absorption lidar (DIAL), with FIG. 3a illustrating the use of on-resonance and off-resonance wavelengths, and FIG. 3b showing the evolution of backscattered power with distance.

The basic approach used for detection is that of differential absorption lidar (DIAL); the basic principle is shown in FIG. 3. Two wavelengths are selected, on and off resonance with a strong absorption line belonging to the chemical species of interest. The wavelengths are selected to minimise spectroscopic interference from other species. The extinction coefficient for each wavelength can be used in Equations 7 and 10 above to calculate the power scattered back to the detector (FIG. 3b). The difference in detected signal at the two wavelengths ($\Delta P = P_{off} - P_{on}$) can be related to the difference between extinction coefficients $\Delta\alpha$ at the two wavelengths (Equations 11 and 12 for the aerosol and extended surface respectively).

$$\Delta\alpha = \frac{\Delta P R}{4 P_T \beta Z_R A_R K} \quad \text{Equation 11}$$

$$\Delta\alpha = \frac{\Delta P \pi R}{\rho P_T A_R K} \quad \text{Equation 12}$$

From FIG. 3, a further assumption is made that the background absorption is constant and equal to $\alpha(v_{off})$; therefore the difference in absorption coefficient between the two wavelengths is equal to the absorption coefficient of the molecule at the on resonance wavelength ($\Delta\alpha = \alpha(v_{abs})$). The off resonance extinction coefficient is the sum of all other species present. This analysis relies upon the absorption terms (i.e. $\alpha(v_{off})$ and $\alpha(v_{on})$) being relatively weak so the exponential term can be expressed as a linear series (exp(-2 $\alpha$R)~1- 2$\alpha$R).

Equations 11 and 12 equate the desired experimental quantity (the extinction coefficients which relate directly to the concentration of the species of interest) to the experimentally measured parameter, the difference in backscattered signal between two wavelengths at a given distance. Conversely, the difference in backscattered signal between the two wavelengths can be expressed in terms of instrumental parameters (e.g. transmitted power, collection efficiency, detector area, diffuse reflectivity/aerosol backscattering, Rayleigh length, extinction coefficients and distance). Ultimately, the smallest value of $\Delta P$ which can be measured is the noise level of the instrument. This value, in turn, defines the smallest possible extinction coefficient difference that can be measured and the ultimate sensitivity of the instrument to the molecule of interest. Equations 11 and 12 can be applied to both direct and heterodyne detection if the appropriate noise terms are included. For active heterodyne detection, the noise is dominated by a combination of speckle noise and local oscillator shot noise. For high backscattering power, speckle noise dominates, and for low backscattering power, the shot noise dominates.

As indicated previously, the basic principle of heterodyne detection is that a signal of interest is mixed non-linearly with a local oscillator at a slightly different frequency. The result of the mixing provides a beat signal which oscillates at the difference frequency but which contains the amplitude and phase information of the high frequency signal. At radio frequencies, electric field can be measured directly to recover this signal, but in the optical domain it is necessary to use a photodetector to produce an electrical signal resulting from the optical signal (mixing is not achieved in this technique by using a nonlinear crystal). This electrical signal (photocurrent) is proportional to the total optical intensity (and hence to the square of the electric field).

As stated above, mixing does not take place in a non-linear crystal—it requires beam alignment so that the beams are mode-matched, which requires the wavefronts to be aligned across the detector with uniform interference, which itself requires the beams to be spatially coherent.

The output signal contains a fixed component, a high frequency component and a beat frequency component—the fixed and high frequency components can be filtered out, leaving the beat frequency component for analysis. In general terms, this can be represented as below:

For received signal $E_{sig} \cos(\omega_{sig} t + \phi)$
and local oscillator signal $E_{LO} \cos(\omega_{LO} t)$
the intensity I, which is proportional to the square of the amplitude, is as follows:

$$I = \underbrace{\frac{E_{sig}^2 + E_{LO}^2}{2}}_{\text{constant component}} + \underbrace{\frac{E_{sig}^2}{2}\cos(2\omega_{sig} t + 2\varphi) + \frac{E_{LO}^2}{2}\cos(2\omega_{LO} t) + E_{sig} E_{LO} \cos((\omega_{sig} + \omega_{LO})t + \varphi)}_{\text{high frequency component}} + \underbrace{E_{sig} E_{LO} \cos((\omega_{sig} - \omega_{LO})t + \varphi)}_{\text{beat component}}$$

The two main noise types found to apply to active heterodyne detection are speckle and shot noise. Speckle noise arises from interference between wavefronts of scattered light when the roughness of the scatterer is comparable to the wavelength of the relevant radiation. It can be reduced by averaging over events which are sufficiently well separated in time or space that they will not be correlated with each other. Shot noise results from the random arrival of photons on to the detector, and the main shot noise contribution will be from the local oscillator.

Heterodyne detection has three distinct advantages over direct detection. High spectral resolution ensures the spectral resolution matches the spectral width of the transmitted beam (a few MHz). The fact that the spectral resolution of the heterodyne system is determined by electronic filtering greatly reduces the contribution of background radiation to the observed signal. In terms of sensitivity, heterodyne detection has a particular advantage of providing the heterodyne gain, especially in the mid infrared where direct detection is significantly less efficient than in the visible or ultra-violet. Equations 11 and 12 relate the minimum detectable concentration to a number of parameters including the minimum detectable power difference between wavelengths corresponding to on and off resonance. $\Delta P$ is equivalent to the noise-equivalent power; in heterodyne detection this is the local oscillator shot noise, while in direct detection it is the thermal background (dark noise). At low levels of received power, the noise in heterodyne detection is several orders of magnitude smaller than in direct detection, which has a substantial impact on the detection limit. In addition, the limited sensitivity of direct detection requires higher signal levels, leading to conditions where speckle noise becomes dominant. Furthermore, higher backscatter signal levels require higher laser powers to be transmitted, which may exceed the maximum possible exposure limits as proscribed by law. Heterodyne detection allows the detection of lower levels of backscattered signal and therefore the use of considerably lower transmitted laser powers becomes feasible.

Figure 4:
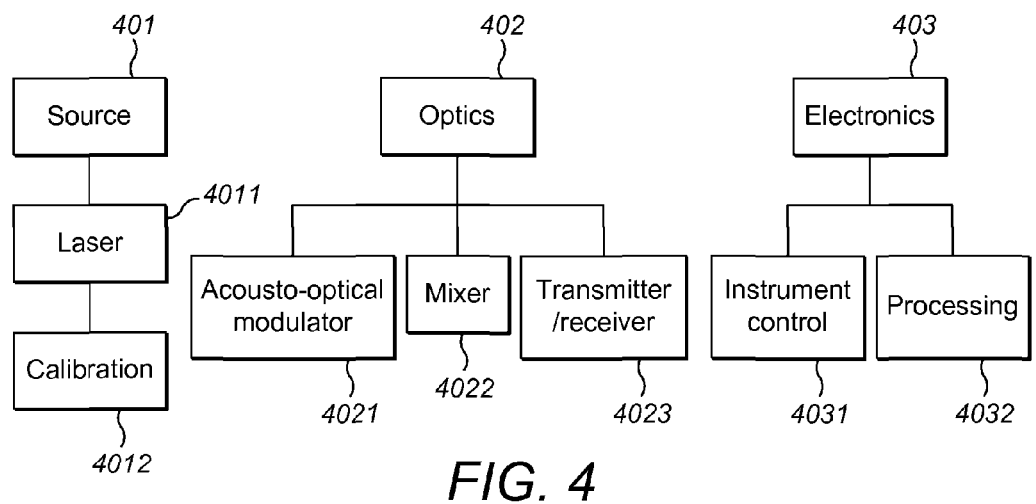
FIG. 4 shows schematically different functional elements of a heterodyne detection system according to an embodiment of the invention.

Different elements of the system will now be described in more detail. FIG. 4 breaks down the overall system into three separate subsystems: the source 401, comprising the laser 4011 itself and its calibration system 4012; the optics 402 routing radiation between the different elements, including the relevant optical elements such as the acousto-optical modulator 4021, the photomixer 4022 and the transmitter and receiver optics 4023; and the electronic subsystem 403 including both instrument control 4031 and processing 4032 (including signal processing and analysis). These subsystems will be treated separately below, for convenience of explanation.

As indicated above, one laser source used in embodiments of the invention is a quantum cascade laser (QCL). This is a semiconductor laser which emits radiation as a result of intersubband transitions in a stack of multiple quantum well heterostructures. QCLs operating are well developed and readily commercially available in the spectral region covering 4 to 20 μm—suppliers include Pranalytica, Alpes Lasers and Daylight Solutions. They typically operate in continuous wave mode close to room temperature with output power up to 50 mW.

The optical gain of QCL structures is inherently broad ($>100 \text{ cm}^{-1}$). Therefore in the simplest configuration—a Fabry-Perot laser in which the quantum cascade material is fabricated as an optical waveguide to form the gain medium, with the ends cleaved to form two parallel mirrors and hence a Fabry-Perot resonator—multi-mode operation is typical, which is unsuitable for high resolution spectroscopic applications.

Single mode operation may be achieved by building a distributed Bragg reflector on top of the laser active zone to prevent operation at other than the desired wavelength. This limits available power and severely limits spectral tuning. Spectral tuning is typically limited to less than 1% of the central laser frequency for continuous wave use, with temperature change used to effect such tuning as is available—a broader range of wavelengths can be accessed in pulsed mode, as "chirping" of the laser wavelength during a pulse can allow scanning of a spectral region.

A preferred solution is to use an external cavity laser. The quantum cascade device here serves as the laser gain medium, but one or both of the waveguide facets has an anti-reflection coating which defeats the cavity action of that waveguide facet. Mirrors external to the device define the optical cavity, which can now include a frequency-selective element such as a diffraction grating to cause the laser to operate in a single mode and to enable continuous tuning over a broad spectral range. The tuning range of such devices is limited only by the gain curve of the QCL, and such devices can be capable of scanning over more than $100 \text{ cm}^{-1}$ in the mid-infrared (i.e. 10% of the central frequency).

While a QCL is a highly suitable choice for embodiments of the invention, other continuously tuneable lasers in the optical ranges of interest could also be used. OPOs and DFG sources can also be obtained which are continuously tuneable in long and medium wavelength infrared. OPO (optical parametric oscillator) sources use an optical resonator and a non-linear optical crystal to convert a pump laser wave into two waves of lower frequency—OPOs are commercially available from companies such as Coherent, Inc. and NKT.Photonics. DFG (difference frequency generations) also use a non-linear crystal, but in this case two near-IR lasers are focussed into a non-linear crystal to generate radiation at the difference frequency—commercial DFG lasers are available from companies such as NovaWave.

To achieve desired sensitivity and selectivity, it is strongly preferred that the laser source is capable of continuously tuning over the entire absorption line/band of the molecule of interest. This cannot be achieved with a conventional DIAL system, which operates at specific predetermined wavelengths. For atmospheric gases (e.g. $CO_2$, $O_3$, etc) under typical atmospheric conditions, absorption lines are of the order 0.1 $cm^{-1}$ full width at half maximum (FWHM) at sea level. In contrast, larger, more complex species (including explosives) can have absorption bands with widths of 10 $cm^{-1}$ or greater. In general, the spectroscopy of explosives and related species is poorly characterised in terms of both band frequencies and widths.

Quantum cascade lasers can be wavelength tuned through current and/or temperature modulation; it is very important to accurately control these two parameters to ensure the frequency stability of the emitted radiation. Commercial temperature and current controllers are available which provide the stability required to operate the QCL in spectroscopic applications—temperature control will be discussed further below.

The small facet size of QCLs results in widely divergent emission of radiation (typically 60 by 40 degrees full angle). Hence a fast, high quality, optic (e.g. an aspheric meniscus) is required to efficiently collimate the radiation at the QCLs output. This optic defines the initial beam size of the collimated laser light (typically <10 mm).

QCLs are highly sensitive to optical feedback (OF) caused by surface reflections from transmissive optical components and the detector. This applies to both DFB and external cavity devices. Relatively small amounts of OF (<60 dB) can perturb the QCL emission and introduce excess noise which is detrimental to heterodyne sensitivity. The use of reflective rather than refractive optics greatly reduces this effect. However, feedback caused by reflection from detector surfaces cannot be so readily eliminated. Hence it is necessary to optically isolate the laser from the detector using a quarter wave-plate, exploiting the polarisation properties of the laser radiation. The quarter wave-plate has to be inserted after the AOM (described below) as the efficiency of the AOM is polarisation dependant (the input beam must be linearly polarised).

Transmission of laser radiation along open paths is restricted in public places through legal exposure limits (100 $mWcm^{-2}$ for eye exposure in the mid-infrared). Therefore an instrument suitable for deployment in public places must comply with these restrictions. A transmitted laser power of 5 to 10 mW will meet safety criteria for eye exposure over all distances. Quantum cascade lasers tend to have relatively low powers (on average up to 100 mW for single mode devices). While this could be problematic in applications such as atmospheric sensing where long range observation (>1 km) is desired, at short ranges (<1 km) this can become an advantage. The $CO_2$ lasers commonly used in atmospheric sensing are capable of producing several Watts of power and need to be transmitted as relatively large diameter beams to meet exposure limits. This in turn requires large optical components, with implications for physical size and cost. In contrast only relatively small optical components are required for QCLs to meet laser safety standards. Moreover, since the transmitted power must remain low to meet safety regulations, heterodyne detection would triumph over direct detection in terms of signal-to-noise ratio. This is because the key discriminator is the backscattered power, which is a function of both distance and transmitted laser power. Less powerful lasers, such as. QCLs, will allow backscattering at short distances to be measured under conditions where the noise associated with the detector is dominant.

It is desirable for the QCL mounting to be extremely stable, as beam alignment is critical for optimal heterodyne mixing efficiency. Sub-wavelength matching of the wavefronts from the local oscillator and the received signal fields is required. It is found that a significant source of instability is the use of a thermoelectric Peltier cooler. A Peltier cooler is the main conventional solution for providing temperature stability to a laser of this type. The present inventors have appreciated that this instability may be addressed by decoupling any motion of the Peltier cooler so that it does not affect the laser position. This approach contributes significantly to achieving the accuracy required for this application.

A preferred laser module provides the following features:
Laser position decoupled from Peltier motion.
Atmospheric pressure operation.
Low temperature operation possible.
Compact size.
Minimisation of the risk of damage to the laser.

Figure 10:
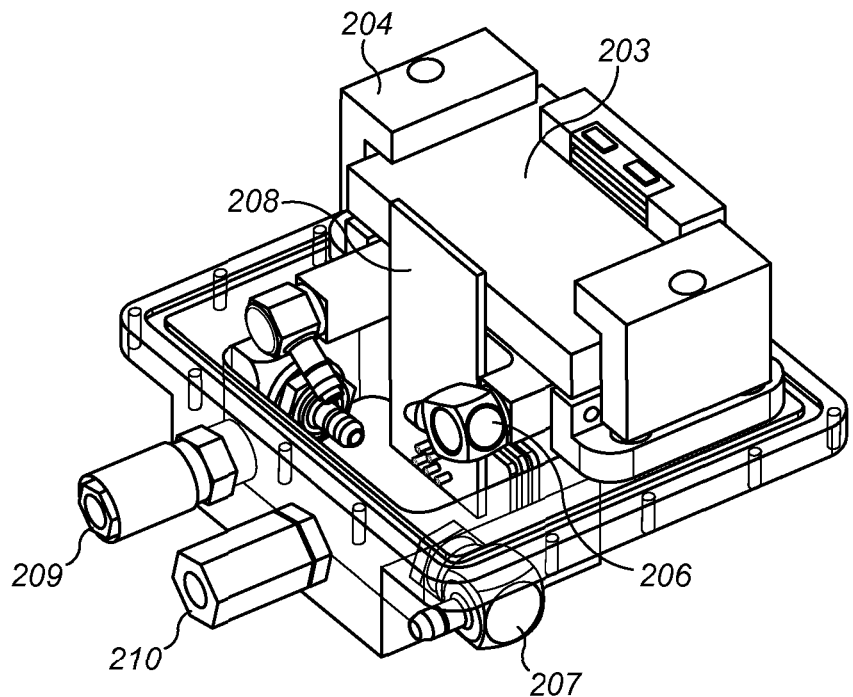
FIG. 10 shows a laser mount for use in embodiments of the invention.
Figure 10:
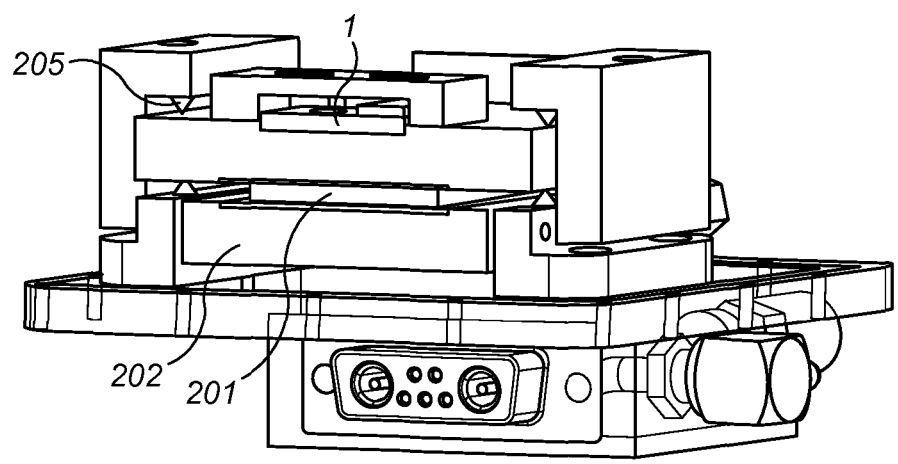

An embodiment of a module which has these features is shown in FIG. 10. The laser source 1—in this case a QCL—is mounted on a cold plate 203 cooled by Peltier cooler 201. The first requirement above implies that the hot side of the Peltier cooler 201 must be free to move, whereas the cooled side must be held static with respect to the main body of the laser module—in this design, the requirement is achieved by suspending the Peltier cooler 201 is suspended from the cold plate 203. A compact method of dissipating heat that is free to move with the Peltier cooler is also provided—this may be a suitably designed heat exchanger 202. A small liquid-cooled heat exchanger 202 sits within the laser housing and extracts the heat from the hot side of the Peltier cooler 201. Attachment of the laser cold plate 203 to the body of the laser module is made with good thermal insulation, using thermally insulating clamps 204 fitted with small conical pin-point contacts 205. To ensure no condensation can occur while operating lasers at low temperature, the module is designed to be purged with a spectroscopically and chemically inert gas. In addition, for maximum safety of the laser, a humidity sensor is installed inside the housing for continuous monitoring of the humidity level and dew point.

The laser module shell is made of aluminium alloy. A single sealing surface compatible with a standard O-ring is used to limit the potential for air leaks. Optical windows are made of barium fluoride, glued onto the module with epoxy. A hermetic connector is mounted at the back of the module to receive the humidity sensor.

When selecting the materials for mounting the laser a trade-off between high thermal insulation and low thermal expansion was necessary. Clamps 204 are made of fibreglass, fitted with ceramic conical pin-point contacts 205 to limit thermal exchange between the laser cold plate 203 and the mounting bracket. Vespel and Macor are also possible materials for this purpose, though fibreglass is found to provide a better overall trade-off.

The laser cold plate 203 and heat exchanger 202 are machined from tellurium copper—pure copper may be used (as may other alloys), but tellurium copper is an effective choice as this has machining benefits over pure coppers with a thermal conductivity that is only slightly lower. To avoid oxidation, leading to a gradual blackening of the surface and loss of thermal performance, the copper parts may be gold coated using an electrochemical bath.

The heat exchanger is preferably made in two parts to allow complex machining, so that the surface exchange between the cooling fluid and the mini-cooler block can be maximized. A folded or labyrinthine flow path may be machined in each half, with the two halves precisely joined, for example by using dowel pins and tin solder.

The laser cold plate 203, Peltier cooler 201 and heat exchanger 202 may be assembled and glued using thermally conducting epoxy. The cold plate 203 can then be integrated with the laser module using the fibreglass clamps 204.

Miniature fittings may be used for both the cooling fluid circuit (for cooling input 206 and cooling feedthrough 207) and for dry gas purging. The former can be mounted on the heat exchanger 202 and connected with Norprene tubing, which is flexible enough to allow free movement of the heat exchanger as the Peltier cooler 201 operates. Right-angle miniature feed-through fittings may be used to pass the cooling fluid through the wall of the laser module without compromising the gas seal of the module. A self-sealing quick connect input valve 209 may be used to attach the purge gas line to the module, and a check valve 210 installed to allow exhaust gas to escape. This arrangement enables purging to be performed quickly and easily.

Electrical contacts may be made using a hybrid sub-D connector, to maintain compact size despite the high current rating required for the Peltier cooler. The connector may be encapsulated in epoxy to prevent air leakage after the connector pins have been soldered on to an electronic board. Contacts to the QCL are provided via a spring-loaded contact pad 208. A thermistor is attached to the laser cold plate 203, the closest possible point to the laser, for temperature regulation.

The laser source is, as previously indicated, continuously tuneable over a range of wavelengths. In principle, this tuning may be by variation of temperature or variation of current. A practical approach to take is to keep the temperature substantially constant using Peltier cooling as described above, and to scan through a frequency range by varying the laser current. One approach which will achieve this is to apply a sawtooth signal to the injection current of the laser source— this will cause the laser frequency to scan across a frequency range defined by the extremes of the sawtooth signal.

A calibration system for the laser source (and hence for the local oscillator) is required. This is provided by one of the outputs from the acousto-optical modulator, which will be described first.

Efficient heterodyne detection (and subsequent electronic filtering and processing) requires the frequencies of the local oscillator and the detected radiation to be different. This also has the beneficial effect of shifting the detection frequency away from low frequency sources of noise. Acousto-optic modulators, used in frequency shifting mode, provide the most efficient way of offsetting the local oscillator frequency with respect to the transmitted beam. Frequency shifts of up to 100 MHz can be obtained with current state of the art commercial systems. In addition, AOM frequency shifting ensures efficient cancellation of any laser frequency drifts without the need of an experimentally complex frequency stabilisation scheme. An exemplary AOM suitable for use in such a system is the IntraAction Corporation model AGM-1003A1, and another is the 1208-G80-3 produced by Isomet.

Figure 5:
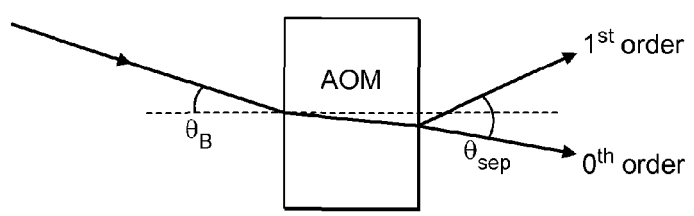
FIG. 5 illustrates the operation of an acousto-optical modulator as used in embodiments of the invention.

FIG. 5 shows a schematic of an AOM operating in frequency shift mode. A crystal (germanium, for example) is excited by a sound wave to create a grating through transverse refractive index modulation. Interaction of the laser radiation with this grating results in the production of frequencies which differ from the original frequency by n.f where n=0, 1, 2, etc, and f is the shift frequency (corresponding to the frequency of the input soundwave). The zeroth (n=0) order retains the original frequency of the input radiation, whereas higher order frequencies (n>0) are shifted in frequency and emerge from the crystal angularly separated. This angular separation allows the frequency shifted radiation to be spatially separated from the unshifted beam.

Commercially available devices are optimised to provide the majority of the output in the first order beam. Typical AOM's have efficiencies of 60% for the production of the first order beam with the remainder (~39%) in the zeroth order beam. A very small fraction (<1%) consists of higher order radiation (i.e. shifted by 200 MHz, 300 MHz, etc.) emitted at greater angular separations. The Bragg angle $\theta_B$ is the required input angle while the zeroth and first order beams are separated by $\theta_{sep}$. Equations 13 and 14 relate these angles to the wavelength $\lambda$, the frequency shift of the AOM, f, and the acoustic velocity of the AOM, v.

$$\theta_B = \frac{\lambda f}{2v} \qquad \text{Equation 13}$$

$$\theta_{sep} = 2\theta_B = \frac{\lambda f}{v} \qquad \text{Equation 14}$$

For a wavelength of 10.6 microns, an offset frequency of 100 MHz and a germanium AOM (v=5500 ms$^{-1}$), the input Bragg angle is 5.5 degrees and the separation angle is 11.0 degrees. Working in the mid-infrared provides a greater degree of separation than would be expected for visible or near-infrared radiation. The separation angle presents a constraint on the minimum size of the AOM module since the zeroth and first order beams must be far enough apart to allow optical components (mirrors, etc.) to be inserted in each individual beam path. The zeroth order beam, although not required for heterodyne detection, will be used to provide calibration for the laser in terms of both power and absolute and relative wavelength.

For an active region of the AOM with an aperture size of 3 mm, given the diameter of the beam emerging from the QCL (~9-10 mm diameter), an optical system is required to match the beam to the AOM aperture. The efficiency of the AOM is approximately 60%. Preferably, the AOM will be placed in the local oscillator beam path to maximise the power available for transmission to the target.

As optical feedback between the detector and the laser can be a major source of noise in a heterodyne instrument. Exploiting the polarisation of the laser can be used to provide a degree of isolation, although care must be taken to ensure linear polarisation at the AOM for maximum efficiency. The presence of the AOM in the optical path may also provide some optical isolation since the first order beam is shifted in frequency from that of the laser; in addition the input angle of the AOM will also reduce the amount of power reflected back to the laser from the detector.

The calibration system will now be described. As indicated above, this uses the zeroth order beam from the AOM. FIG. 8 illustrates a calibration arrangement using this zeroth order beam. for power monitoring and spectral calibration of the local oscillator beam. Flat mirrors mounted on flip-mounts 23 are used to provide separate beam paths for relative (etalon 22) and absolute frequency (gas cell 21) calibration. The contents of the gas cell 21 will be determined by the wavelength of the laser. A low pressure gas will exhibit an absorption line dominated by Doppler broadening (ca. 50 MHz), allowing the frequency of the laser to be determined in absolute terms. The beam is focused onto a Peltier-cooled photodiode detector 24. This detector can have a considerably lower specification than that required for heterodyne photomixing. The flip mounts 23 can be configured to pass the radiation through either the reference gas cell (absolute frequency calibration) or the etalon (relative frequency calibration). Absolute power measurements can be performed by incorporating additional flip mounts to divert the beam around the reference cell and etalon, or by physically removing either the reference cell or the etalon from the optical path. Alternatively, the laser power could be monitored using the portion of the local oscillator which is transmitted by the beam splitter used to provide the input to the photomixer—however, the latter would require an additional detector.

Although QCLs provide continuous tuning, the output power of the laser may vary greatly over the spectral tuning range. Experimentally, knowledge of the variation in laser power during laser tuning allows the heterodyne signal to be corrected. However, due to the saturation effects that can occur in photomixers, there is an optimum level of LO power that will ensure the heterodyne receiver operates at close to the shot noise detection limit. Variations in LO power will lead to changes in the measurement signal-to-noise ration, so stabilizing the local oscillator power would be beneficial.

A feedback loop from the LO power monitor could be used to control the current supplied to the QCL. However, modifying the laser injection current affects the laser frequency therefore such a scheme is not appropriate for heterodyne detection or for spectroscopic applications. An alternative is to exploit the inherent polarisation of the laser source to achieve power stabilization for the laser. Inserting a polarizer in the QCL beam will allow control of the power transmitted by rotating the polarizer axis. Installing a feedback loop between the angle of the polariser and the power monitor allows the laser power to be kept constant over the whole spectral scan.

Figure 12:
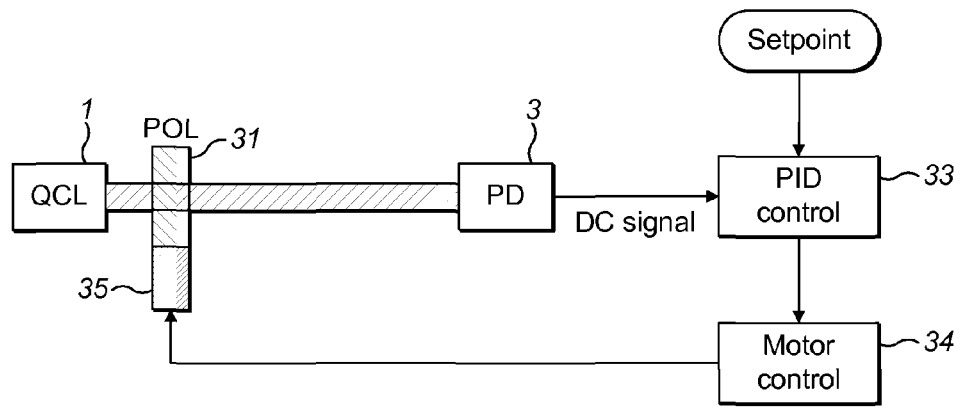
FIG. 12 shows an exemplary control system for providing feedback to control the power of the laser source.

This approach is shown in FIG. 12. The stabilization of laser power exploits the polarization properties of QCL radiation. Using a polariser 31, the laser power can be attenuated in a controlled manner through modification of the angle between the polariser axis and the laser polarization. Theoretically the transmitted power varies as the square of the cosine of this angle. Contrary to stabilization schemes relying on laser injection current, the use of a polarizer does not affect the laser frequency.

A polariser 31, once installed on a motorized rotation stage 35, can be controlled by an external voltage signal. A relationship between the command voltage and the polarizer attenuation can be established creating a voltage-controlled attenuator. Since such an approach relies on mechanical motion, it will be slower than modulation speeds achievable through laser injection current. It is however, a cost and time effective way of implementing this aspect of the system with commercial off-the-shelf components. The inventors have appreciated that high speed is not a requirement as far as laser heterodyne systems are concerned. A similar approach could be employed using mid-infrared saturable absorbers—this would allow faster response times, but these components are not currently readily available at reasonable cost.

In heterodyne detection, only the AC coupled signal from a high-speed detector contains information on the intermediate frequencies that carry the spectral information. At power levels below saturation, the DC coupled component is linearly proportional to the LO power and can be used as a power monitor input for a proportional-integral-derivative (PID) system. The PID system feeds back to the polarization state and thereby maintains the high-speed detector DC signal at a constant level, determined by a set-point chosen by the operator. The principles of the control system are as illustrated in FIG. 12.

In an exemplary arrangement, the polarizer 31 may be a wire grid on a Barium Fluoride substrate, mounted on a high-speed motorized rotation stage 35 connected to a computer control interface 34. A PID controller 33 is responsive to the DC coupled component from the heterodyne detector 3. The PID controller 33 is a readily commercially available component, and is used to provide the feedback signal to the motorized stage control interface. This approach can achieve a response time of 50 ms, and is found to be effective to track a frequency scan driven by a sawtooth signal applied to the injection current of the laser.

PID control provides a relatively simple way of minimising the influence of disturbances on a system. In this scheme, the output of a PID system is used to alter some physical parameter in such a way as to minimise the difference between a measured value and a required set-point. The basic PID relationship is given in Equation 9. $V_{OUT}$ is the output voltage delivered by the controller, P is the proportional gain term, I is the integral gain term, D is the differential gain term and $V_0$ is a constant voltage offset. The term $\epsilon$ represents the error signal that corresponds to the difference between the measured signal and the set-point chosen by the user.

$$V_{OUT} = P\left\{\varepsilon + I\int edt + D\frac{d\varepsilon}{dt}\right\} + V_0 \qquad \text{Equation 15}$$

Optimum control is achieved by tuning the P, I, and D parameters of Equation 15. The proportional term is a gain term linearly scaling the magnitude of the feedback voltage to that of the error. The integral term compensates for any drift of the error over time and usually affects the precision of the feedback. The derivative term is a measure of the rate of change of the error signal $\epsilon$ and compensates for rapid changes. When a high level of stability is required, this parameter is usually set to zero.

In the embodiment described here, the control parameter is the voltage delivered by the detector, which is linearly proportional to the laser power. The feedback loop is established by connecting the PID controller output to the analog input of the rotation stage. Thus, the error signal determines the polarizer position and therefore controlled the transmitted power. It may be necessary to introduce an offset in the PID output to allow bipolar control. The optimum PID parameters for the system may be determined empirically.

Figure 6A:
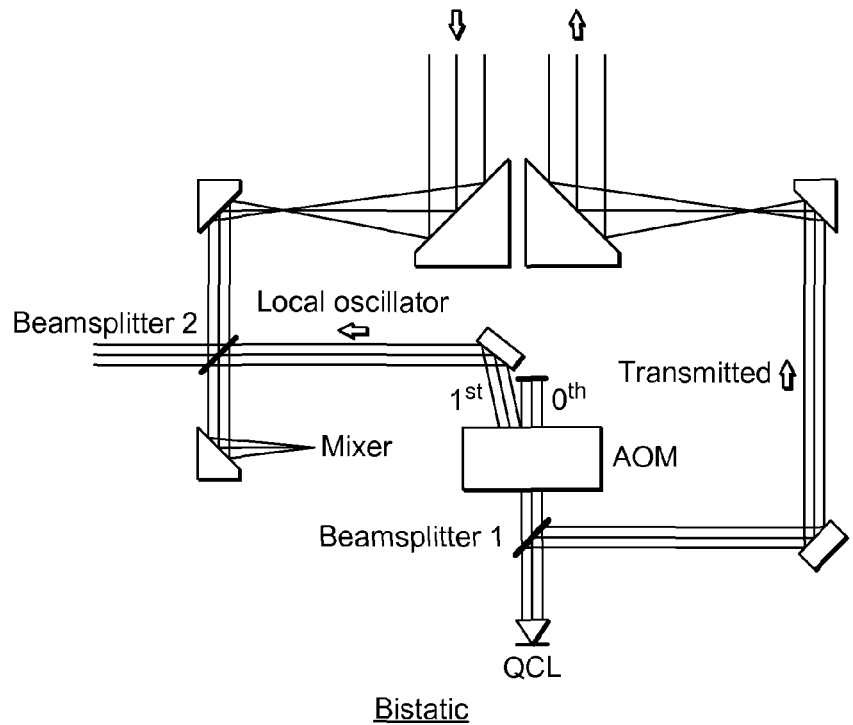
FIG. 6a shows a bistatic optical configuration and FIG. 6b shows a monostatic optical configuration suitable for use in active heterodyne detection systems according to embodiments of the invention.
Figure 6B:
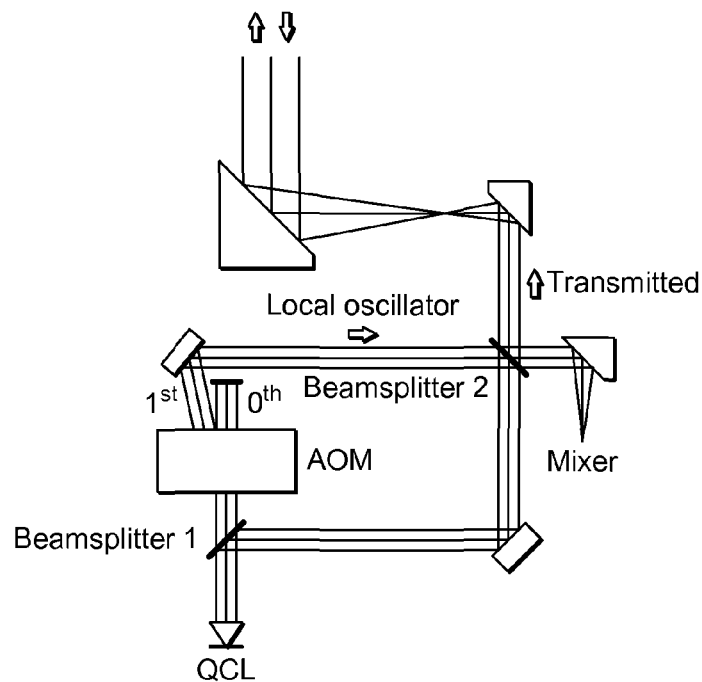

As is shown in FIG. 6, two geometries are possible for the transmitter/receiver assembly. The optics used are 90 degree off-axis parabolic mirrors (OAPM). The bistatic geometry has separate optics for transmission and reception, while a single optic performs both tasks in the monostatic configuration. This suggests that a monostatic configuration offers a simpler, cheaper and more compact design. However, there are other considerations; the transmitted and backscattered radiation must be spatially separated before mixing with the local oscillator beam. To achieve this in the monostatic configuration additional optical components will be necessary. In the bistatic case, the backscattered radiation is already separated from the transmitted radiation by the optical arrangement. The two approaches can be combined, but only by making the components significantly larger to allow for separation of beams.

Since the transmitted and scattered radiations are at the same wavelength, the principal means to separate them (or to combine beams for heterodyne mixing) are beam splitters (partially reflective optics). In the monostatic case, beam splitters must be placed in the path of both beams, with the complication that maximising the transmission through the beam splitter of the backscattered radiation minimises the amount of power that can be transmitted towards the target (and vice versa). The optimum situation is achieved with a 50% transmitting/reflecting beam splitter, corresponding to a reduction by a factor of 4 in the backscattered signal at the detector. The reduction factor is proportional to the transmitted power and to the reflectance of the beam splitter.

An alternative configuration makes use of the polarisation of the laser to selectively reflect/transmit the transmitted/backscattered radiation. The linear polarisation of the laser is converted to circular polarisation by a quarter-wave plate; backscattering from a target inverts the circular polarisation (i.e. from right circularly polarised to left). The quarter-wave plate converts the backscattered radiation into a linear polarisation which is perpendicular to the transmitted beam. A polarising beam splitter (usually set at the Brewster angle) can be used to reflect the transmitted beam and allow the backscattered radiation to pass through (or vice versa). This scheme relies on the radiation preserving a degree of polarisation during its passage through the atmosphere and interaction with the target. Scrambling of the polarisation will result in reduced throughput of the backscattered radiation; if the polarisation is totally randomised, then the polarising beam splitter will act effectively as a 50% beam splitter (as in the non-polarising case). However, it will allow very efficient transmission of the main laser beam. The reduction factor will be less than or equal to two depending on the degree of polarization scrambling caused by the scattering process.

FIG. 6 shows schematically bistatic and monostatic configurations. Constraints on the system include the efficiency of the AOM (~60%) and the output power of the QCL (40 mW maximum). For efficient heterodyne detection the local oscillator power at the detector is preferably approximately 1 mW. The power in the local oscillator beam at the detector is determined by the transmittance of the two beam splitters and the efficiency of the AOM. In the bistatic case the power of the transmitted beam is determined by the reflectance of the first beam splitter. In the monostatic configuration there is an additional reduction in transmitted power depending on the transmittance of the second beam splitter. While either approach can be employed, analysis shows that the bistatic system has a much higher fraction of backscattered radiation transmitted to the detector than the monostatic configuration.

A disadvantage of the bistatic system is that the field-of-view of the detector may not overlap perfectly with the transmitted laser beam. In the worst case, the overlap factor O(R) will depend greatly on the distance from the target; this problem is particularly evident at short ranges with separate transmitter and receiver optical systems. Assuming that the laser spot size at a particular distance matches the heterodyne field of view (i.e. both spots are circular and of the same diameter), the overlap function can be readily calculated. In a practical system, the overlap may be significantly reduced at a range of less than 200 m (very significantly reduced at less than 50 m), but this can be addressed by allowing allow the transmitter (or receiver) optic to tilt to some degree. The tilt angle required to spatially overlap the two beams depend on the distance R to the target and the separation S of the two optics. At a distance of 100 m and a separation of 8 cm, the required tilt angle is very small (ca. 0.045 degrees). Tilting both optics simultaneously requires each optic to tilt by only half this angle. Such tilt angles can be achieved using the manual adjustors of the optical mounts. An alternative is to use motorised actuators to control (via a computer) the tilt angle.

The use of continuous wave laser sources does not immediately allow range resolved information to be obtained. However, approaches have been developed which allow range information to be determined by controlling (and adjusting) the focal position of the transmitted radiation. Laser focusing conditions can be controlled using two optics separated by a distance slightly greater than the sum of their focal lengths; a separation equal to the sum of the focal lengths leads to a confocal arrangement where the outgoing beam is collimated (i.e. with a focal point at infinity). Practically, the focal length of the optic will be restricted; hence, reduction of the initial spot size is the principal means of increasing the range to the final focal point. However, a small spot size implies a high degree of beam divergence which means that the beam at the optic may exceed the diameter of the optic, resulting in a significant waste of laser power. The combination of small spot size with a long focal length places a requirement on the optic such that it is large enough to accommodate the beam.

The need to reduce optical feedback to the laser requires the exclusive use of reflective optics. Aspheric mirrors (including off-axis parabolic mirrors) remain astigmatic only in a confocal arrangement. However, as the transmitter's role is purely to illuminate the target, no imaging requirements have to be taken into consideration, there are no constraints on the quality of the wavefronts, and the OAPM can be adjusted freely to set the position of the focus.

An achromatic optical arrangement using only reflective optics is more alignment-critical than one based on refractive optics (e.g. lenses). However, it has an additional advantage, which is that the system can be monitored and aligned using visible radiation, as for reflective optics the behaviour of radiation in the system is largely wavelength independent. Reflective optics are also typically much lower in cost than equivalent refractive optics.

The visible output (ca. 600 nm) of diode lasers can be incorporated into the receiver/transmitter module by using dichroic mirrors or by using "flip"-mounts which can be inserted or removed from the beam as desired. Flip-mounts are cheaper, and will not influence the power of the infrared beam when removed from the beam's path. However, the action of inserting and removing the mount may result in the misalignment of the visible beam relative to the infrared. Dichroic mirrors (fully reflective at visible wavelengths and fully transmitting at infrared frequencies) are a more expensive option, but would form a permanent part of the optical system with minimal problems with misalignment over time.

The heterodyne configuration requires the mixing of the local oscillator beam with the backscattered signal beam. The quality of the mixing (phase front matching) will directly impact the signal-to-noise ratio of the measurements. FIG. 7 shows alternative methods to implement the mixing which differ in the way the two beams are mixed at the photodetector: as parallel beams (FIG. 7a) or as convergent beams (FIG. 7b)

The different configurations have the following main similarities:
- A LO path emerging from the QCL, collimated by a high numerical aperture lens, and imaged onto the photomixer.
- A transmitter path also emerging from the QCL, collimated by the lens, and directed to the target via an afocal expander, A receiver path, where the backscattered radiation is collected by an afocal de-magnifying telescope, and focused onto the photomixer.

The parallel configuration uses the same beam splitter to separate the LO and transmitted radiation and then to recombine the LO received radiation. This is the most obvious way of superimposing the two beams at the detector, but the system will also need to accommodate the AOM. As the AOM needs to be in the LO path, an extra beam splitter is required. Given the entrance aperture of the AOM (~3 mm), the beam needs further demagnification. This can be achieved with a reflective afocal expander with confocal off-axis parabolas, but with a lower angle of incidence for compactness and in particular higher tolerances to misalignment. This afocal system also reduces the polarisation splitting.

Convergent mixing involves a more complex optical design than the parallel arrangement. However, because of the existence of conjugated intermediate images, it offers more flexibility and control over the optical alignment. The infrared beam quality may also be less sensitive to beam splitter surface imperfections. In addition to the lateral shift of the beam (50% of the beam splitter thickness at 45 degree incidence on a ZnSe plate) an axial defocus will occur which may produce spherical aberrations and astigmatism. This can be compensated by re-adjusting component separation and/or by adding a compensation plate possessing the same properties as the beam splitter placed at an anti-symmetric position. However, when the field of view is small the gain from the compensation may not be significant compared to increased optical feedback caused by introducing an additional transmissive optical component. To integrate the AOM similar modifications are required as in the parallel mixing case. The use of an ellipsoid mirror for final focusing onto the detector surface has both advantages and disadvantages: it is intrinsically more difficult to co-align the image of the detector with the two diverging beams in the object space of the ellipsoid but the sequence of a parabola and an ellipsoid leads to the standard Gregorian off-axis configuration, which has more tolerance than a single parabola.

Careful consideration of the afocal receiver system is desirable, particularly where the target is expected to be at a finite distance (tens to hundreds of meters), with the receiver is optimized for a flat incoming wavefront. If the target is too close then it will be out of focus. To accommodate a close target (closer than, say, 500 m) compensating adjustments of the axial separation between mirrors of the afocal telescope should be made, in an analogous way to the variable ranging capability of the transmitter set out above.

The presence of a refringent parallel plate window in front of the detector will create an axial defocus. One can expect that within the detector assembly the detector-window separation will be fixed and therefore compensation can be included in the design of the detector. For a ZnSe window of thickness t millimeters the defocusing will be approximately 0.585×t. This defocusing distance will be larger if a detector tilt is introduced in order to reduce optical feedback.

The sensitivity of a heterodyne instrument is ultimately determined by the quality of the photomixer (and its associated electronics) used to detect the heterodyne signal. The fundamental limit of the heterodyne detection systems sensitivity is reached when the noise recorded by the photomixer is solely determined by the shot noise from the local oscillator; sources of noise associated with the detector and its amplifier assembly must be reduced to below this shot noise level. Up until now, liquid-nitrogen cooled Mercury Cadmium Telluride (MCT) photodiodes have been used for heterodyne detection. Some manufacturers (Fermionics, Kolmar, Judson and Hamamatsu) can offer high-speed MCT photodiodes that are optimized for heterodyne detection, with Kolmar providing photodiodes operating up to few hundreds of megahertz bandwidth. Alternative technologies for high-speed detection in the mid infrared are also available. These include quantum well infrared detectors (QWIPs), quantum cascade detectors (QCDs) and avalanche photodiodes (APDs).

The electronics system will now be considered. For spectroscopic applications, frequency stability of the laser source is essential for maximum sensitivity and reproducibility. The wavelength of a QCL is determined by its temperature and the current applied to it. Therefore the temperature and current must be controlled to a high degree of accuracy. A typical mid-infrared QCL has tuning rates with respect to current and temperature of ~4 $cm^{-1}A^{-1}$ and ~0.05 to 0.1 $cm^{-1}K^{-1}$ respectively. An optical frequency stability of 1 MHz (0.00003 $cm^{-1}$) requires a current stability of 0.001% and temperature stability of 0.03%. At 273 K and 1 A this corresponds to a stability of $10^{-5}$ A (10 μA) and 0.08 K (80 mK). Therefore a high precision current source and temperature controller are required to operate the QCL.

The laser can be scanned in frequency rapidly using current ramping or more slowly using temperature tuning. For trace detection of materials for real-time use, rapid tuning is clearly preferable. A waveform generator is required to produce the correct shape for a tuning ramp; the slope of the ramp will be determined by the tuning characteristics of the laser, the spectral range required and the acquisition time. In addition to the tuning ramp, laser wavelength modulation will be performed by applying a sinusoidal current modulation to the laser injection current. Signals are visualized using a fast digital oscilloscope to optimized both optical adjustments and synchronization.

The AOM is controlled by a RF synthesizer, which can be either fixed frequency or adjustable. Though a fixed frequency should be enough to generate the frequency shifting, a variable frequency can offer more flexibility and additional modulation features: e.g. wavelength modulation immune from power modulation and high frequency modulation.

Mechanical control is provided by stepped motors and piezoelectric actuators interfaced with a computer.

Acquisition of detector signals will be made using a NI DAQ-Card multi-function card, equipped with analog and digital inputs and outputs. A lock in amplifier is used for amplitude and/or wavelength demodulation.

Of particular importance is the signal from the photomixer, and the nature of the processing line will depend on the type of photomixer used. In general, the photomixer back end will incorporate the following elements:

A bias tee so that the photomixer can be reverse-biased to widen the bandwidth.

An AC/DC splitter so that the DC current can be monitored while the AC component is directed to the amplification stage.

Amplifiers for the heterodyne signal. Well matched, transimpedance amplifiers are reported to give the best performance. A second voltage amplification stage might be necessary to bring the gain up to 50 to 60 dB. Following amplification the heterodyne signal can be analyzed to determine phase and amplitude.

For low level of signals, when using the frequency scanning capabilities of the LO, a fixed bandpass filter (defining the instrument resolution) followed by a Schottky RF detector is required at the output of the amplification chain. The RF signal is demodulated by the lock-in amplifier.

Additional processing of the signal may be used to reduce speckle noise, baseline correction, spectral calibration, etc.

In a preferred approach, the Optimum Estimation Method (OEM) is used. Publicly available algorithms may be used to take this approach to recovery of state information from noisy data. OEM is described in detail in "Inverse Methods for Atmosphere Sounding Theory and Practice, Series on Atmospheric, Oceanic and Planetary Physics—Vol. 2", Clive D. Rodgers, World Scientific, 2000. The basic theoretical approach is as set out below:

The parameters to fit are concatenated into a vector $\vec{x}$ called the state vector, of dimension n. The experimental data makes a vector $\vec{y}$ called the measurement vector, of dimension m.

The first step consists of building the forward model, which contains all the physics known about the problem. The forward model relates the state vector $\vec{x}$, to the measurement vector $\vec{y}$, according to:

$$\vec{y} = F(\vec{x}) + \vec{\epsilon} \qquad \text{Equation 16}$$

where the function F represents the forward model, and $\vec{\epsilon}$ is the error vector accounting for the mismatch between the model's results and the measurements. The retrieval problem consists of inverting the problem and solving for $\vec{x}$, knowing $\vec{y}$.

As indicated above, the forward model contains the physics of the whole process, including illumination, scattering and detection. This physics has been set out above earlier in this description of specific embodiments. In developing the forward model, the backscattered power which will be available within the field of view of the instrument's collection aperture is first determined—this will be independent of the detection scenario. This provides an input into the next stage which depends on the receiver properties, and the heterodyne signal is modelled from these receiver properties. Noise sources may also be modelled to provide a quantitative determination of how noise affects the system. The outputs of the forward model comprise a modelled heterodyne signal with noise.

To constraint the inverse problem further, a set of a priori data on the parameters to fit is necessary. Those will include all the a priori knowledge we have on the parameters being retrieved. The a priori data forms the a priori vector $\vec{x}_a$, and the uncertainty on the a priori data are incorporated into the a priori covariance matrix $s_a$. In addition, the imperfection of the measurements is accounted for through the measurement covariance matrix $S_\epsilon$.

If we assume that the measurement complexity is such as the central limit theorem applies, the error statistics will be gaussian, and in this case the problem will follow theorems of Bayesian information, and inverting the problem becomes the minimization of a cost function $\chi^2$ defined as:

$$\chi^2 = [\vec{y} - F(\vec{x}_n)] \cdot S_\epsilon^{-1} \cdot [\vec{y} - F(\vec{x}_n)]^T + [\vec{x}_a - \vec{x}_n] \cdot S_a^{-1} \cdot [\vec{x}_a - \vec{x}_n]^T. \qquad \text{Equation 17}$$

When $\chi^2$ is minimized, $\vec{x}_n$ is the best estimator of $\vec{x}$.

For a moderately non-linear inversion problem, a local linearization of Eq. 16 becomes:

$$\vec{y} = K \cdot \vec{x} + \vec{\epsilon}, \qquad \text{(B3)}$$

where K is the jacobian matrix also called the set of weighting functions. The iterative Levenberg-Marquard approach is used to converge towards the best estimate $\vec{x}_n$, minimizing $\chi^2$ according to the following algorithm relating the state vector for the iteration i+1 to the one from the iteration i:

$$\vec{x}_{i+1} = \vec{x}_i + [(1-\lambda)S_a^{-1} + K_i^T \cdot S_\epsilon^T \cdot K_i]^{-1} \cdot [K_i^T \cdot S_\epsilon^{-1} \cdot (\vec{y}_i - F(\vec{x}_i)) + S_a^{-1} \cdot (\vec{x}_a - \vec{x}_i)]. \qquad \text{Equation 18}$$

$\lambda$ is the Levenberg-Marquard dampening parameter, and will be set to offer a good trade off between convergence speed and accuracy of the estimation.

Figure 9:
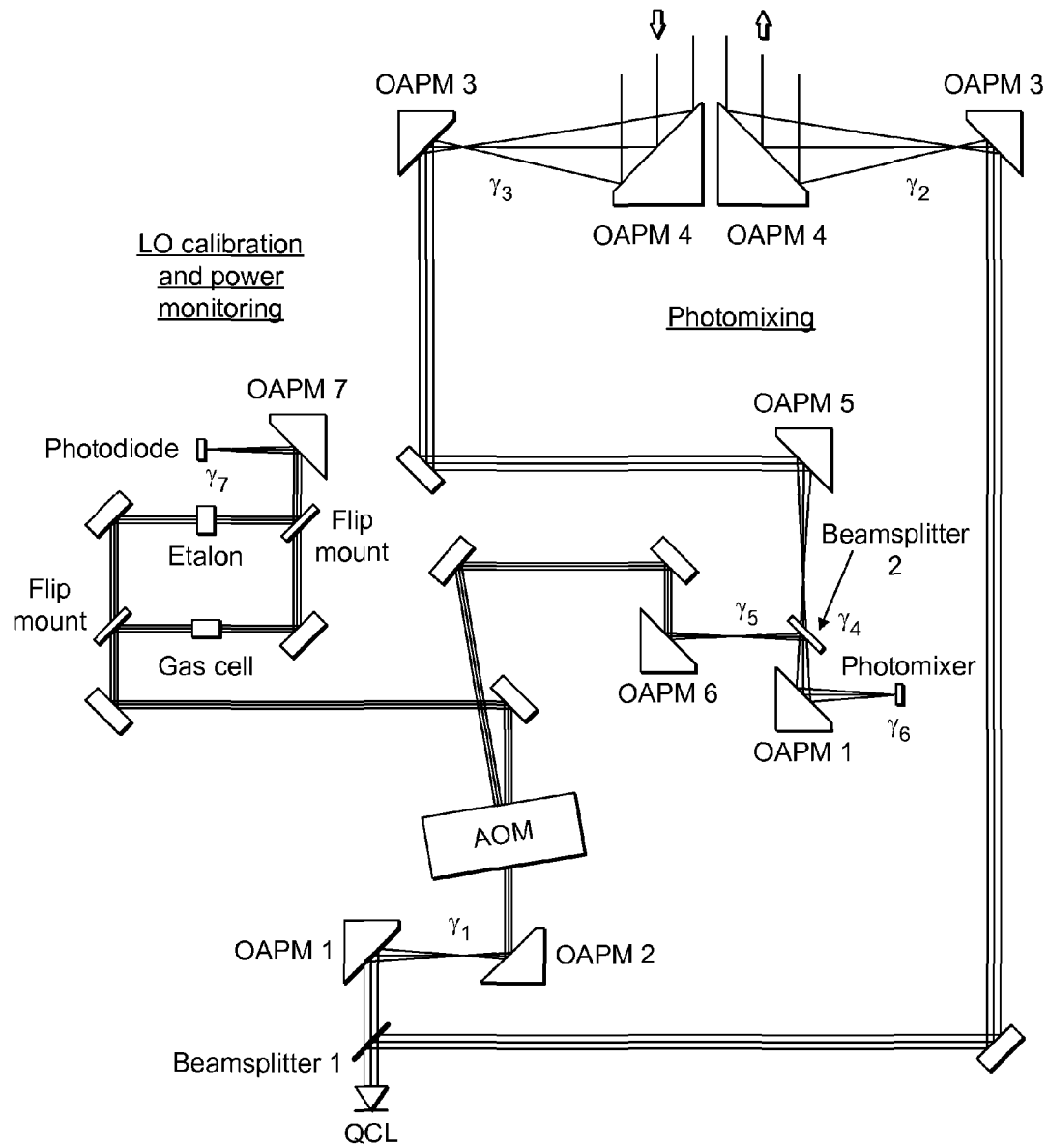
FIG. 9 shows a full exemplary optical system for an active heterodyne detection system according to an embodiment of the invention.

A full system is shown schematically in FIG. 9. In the schematic, 90 degree off-axis optics has been used for convenience. In a real instrument, 30 degree optics could be used to relax alignment tolerances and to reduce the overall footprint of the instrument. The instrument can be made more compact by decreasing the spacing of the optical mounts wherever the beam is collimated. Physical constraints on focusing elements remain. Space can also be gained by separating the beams emerging from the AOM at a point closer to the AOM output by using custom-designed optics (e.g. D-shaped mirrors). The instrument may advantageously be split over two decks: the lower deck containing the transmission/reception optics, while the upper deck contains the rest of the instrument. The ultimate limits on size are the effective focal lengths of the mirrors of the transmitter/receiver section. The use of 30° off-axis optics allows the use of longer focal lengths in a compact design.

Figure 11:
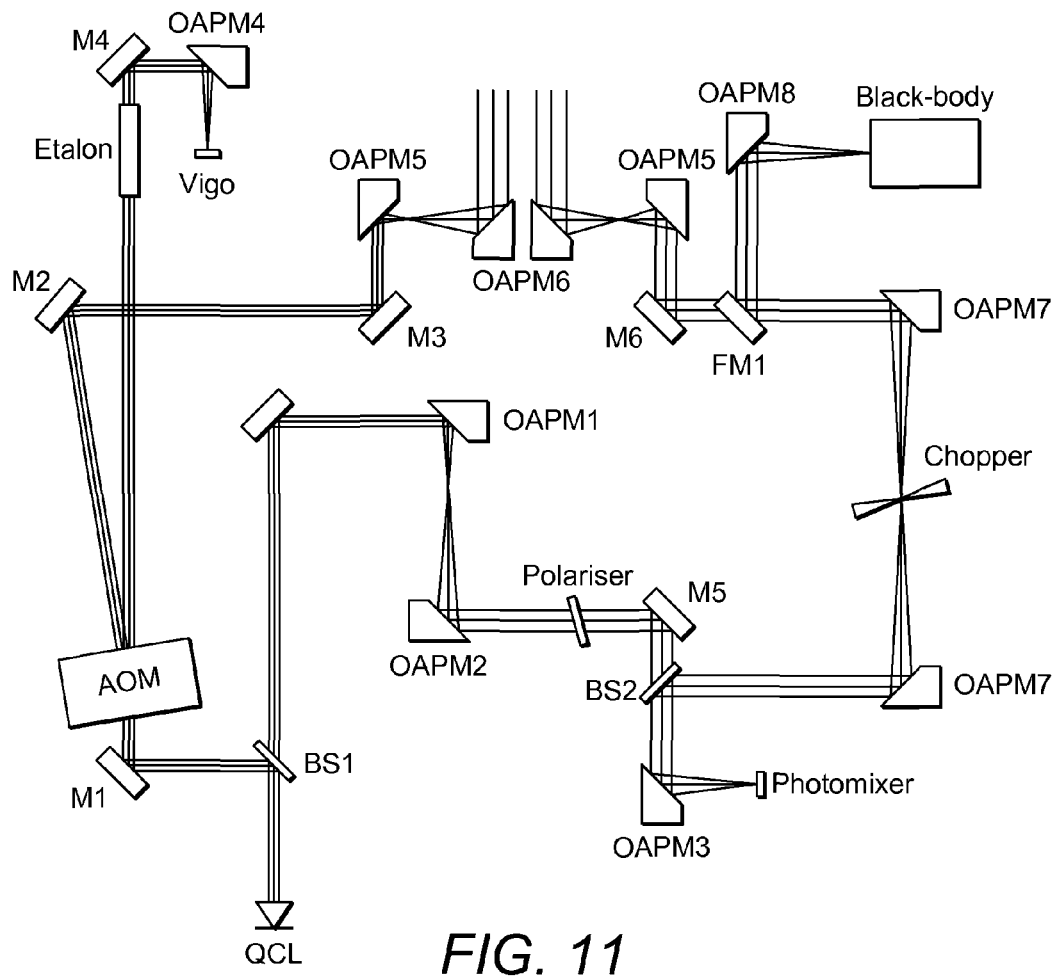
FIG. 11 shows an alternative full optical system for an active heterodyne detection system according to an embodiment of the invention.

An alternative optical layout is shown in FIG. 11. In this arrangement, the frequency shift is applied to the light for illuminating the target, rather than to the local oscillator. This allows the local oscillator radiation to be directed directly from the first beamsplitter to the photomixer, and the zeroth order output of the acousto-optical modulator to be used for calibration. As the local oscillator signal is a principal source of noise, this can improve the overall performance of the instrument, as less noise is introduced in the local oscillator path. The first order output of the acousto-optical modulator is then used for transmission to the target.

The approach set out in FIG. 11 is particularly suitable for using an approach to reducing laser speckle that is taught in the applicant's copending UK Patent Application No. 1221677.6 entitled "Method and Apparatus for Reducing Speckle Noise in an Optical System" and originally filed on 30 Nov. 2012. In this approach, an optical component is dithered to vary the position of illumination of the target—in the arrangement shown in FIG. 11, any of the optical components between the AOM and the target (M2, M3, OAPM5 or OAPM6) can be dithered in this way. This approach can also be used in other arrangements described—most generally for example by dithering mirror 9 shown in FIG. 1. The disclosure of UK Patent Application No. 1221677.6 is disclosed herein to the fullest extent permitted by applicable law.

Figure 13A:
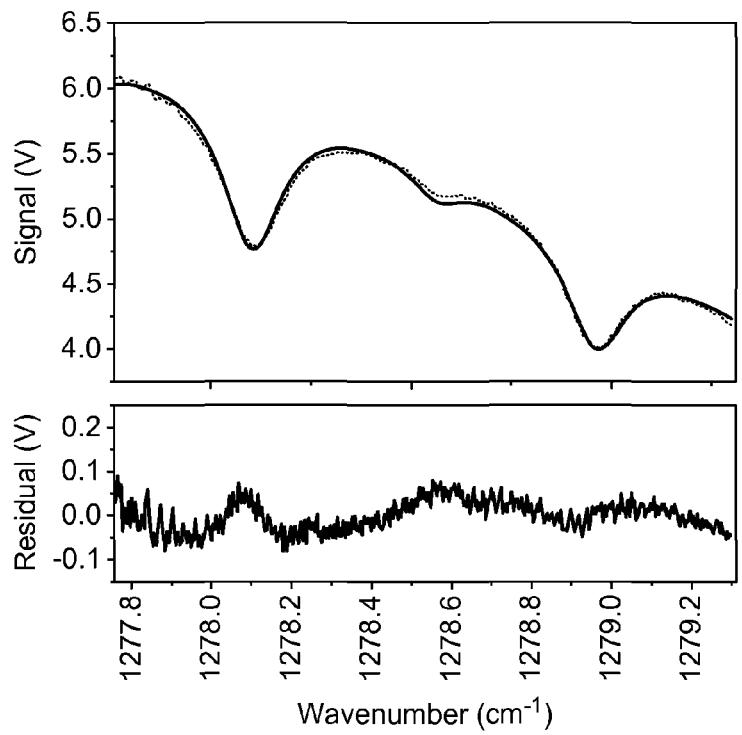
FIGS. 13a and 13b show experimental results for a detection system according to an embodiment of the invention for detection of gaseous samples in a gas cell.
Figure 13B:
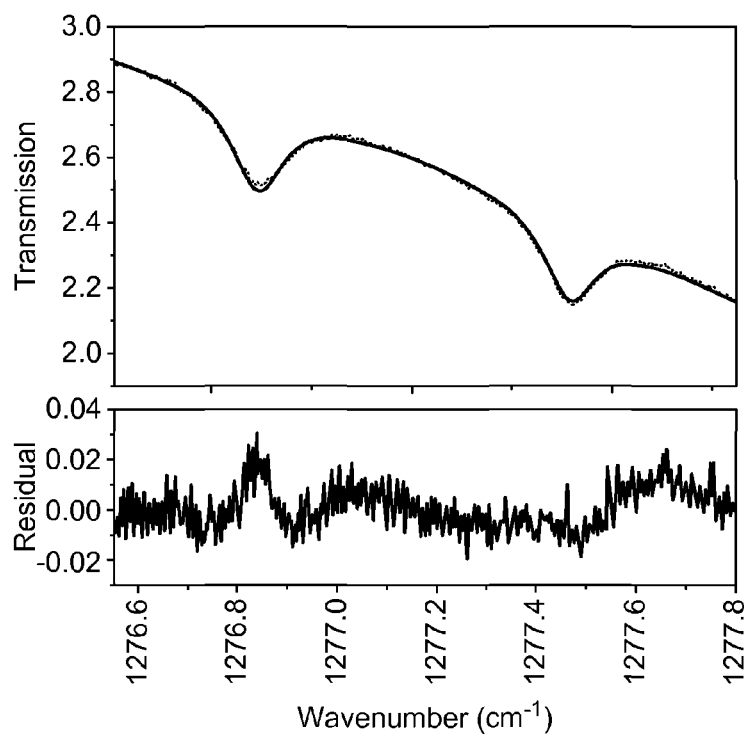
Figure 14A:
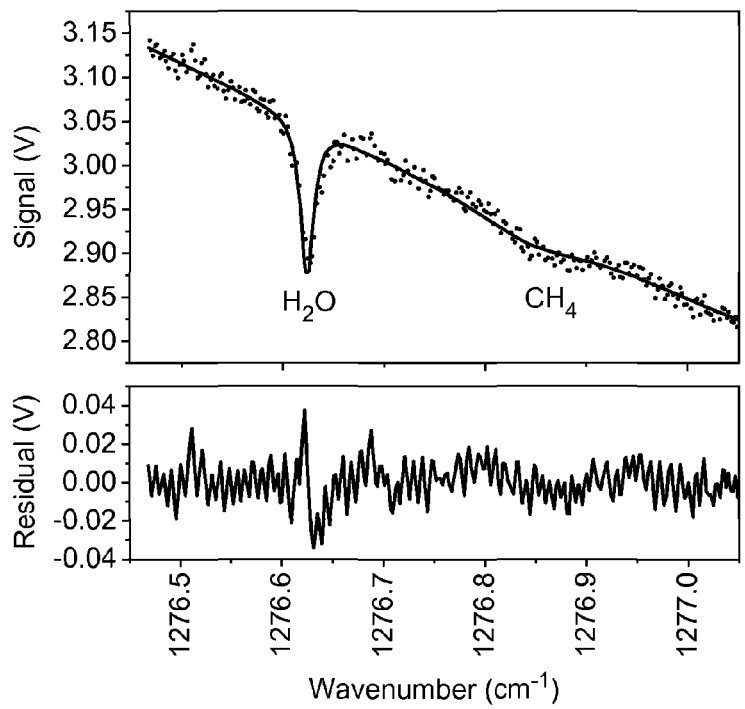
FIGS. 14a and 14b show experimental results for a detection system according to an embodiment of the invention for detection of atmospheric samples.
Figure 14B:
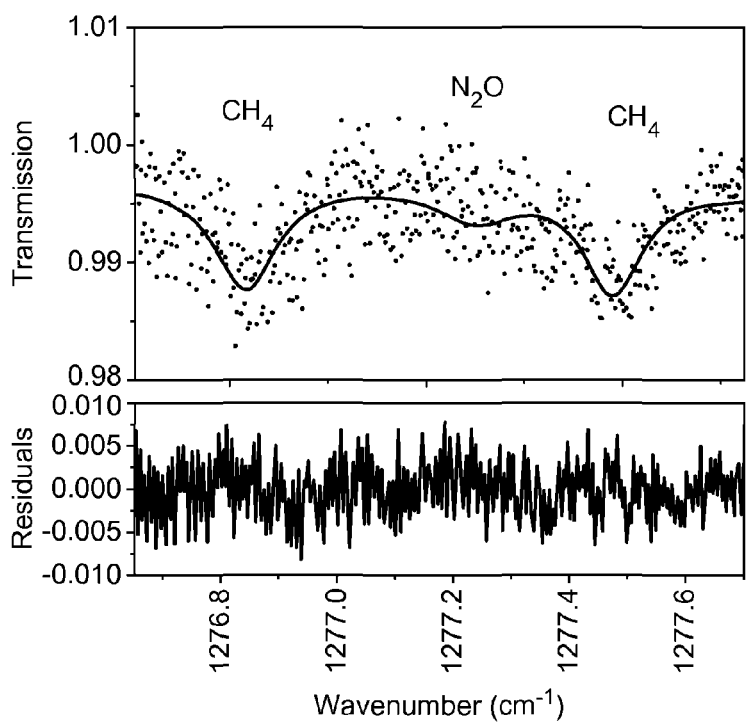

Experimental results are shown in FIGS. 13 and 14. FIGS. 13*a* and 13*b* show results from remote detection of gas in a gas cell containing a known concentration of gas located between the system and a target. FIGS. 14*a* and 14*b* show results with the gas cell removed, and provide detection of atmospheric gas. All measurements were taken using a mechanical chopper with an integration time of 100 ms to integrate signal and a double-sided heterodyne bandwidth of 1.6 MHz. A sawtooth ramp of 200 mA producing a 1.8 cm$^{-1}$ frequency sweep at a frequency of 0.01 Hz was applied to the laser current. The local oscillator power was maintained at the optimum level throughout the scan by using the active power stabilisation system described above. A roughened Aluminium target at a distance of 5.5 m was used.

The metal gas cell was filled with a mixture of first $N_2O$ and then $CH_4$ in 1 atmosphere of dry nitrogen gas. The nominal concentration was 1000±2.5 ppm. Absorption spectra are obtained for $N_2O$ (FIG. 13a) and $CH_4$ (FIG. 13b). In the spectra regions selected, there are no significant water absorption features. The upper panels show the experimental spectra (points) and fitted spectra using the OEM algorithm (continuous line). The lower panels show the residual between the experimental and fitted spectra.

Both $N_2O$ and $CH_4$ exist naturally in the atmosphere with typical concentrations of 0.32 ppm ($N_2O$) and 1.8 ppm ($CH_4$) respectively. Although these concentrations are considerably lower than those used in the cell, the long path length (12.94 m) allows the natural abundance to be observed when the cell is removed. The path length includes the distance to and from the target and the distance the transmitted and backscattered beams travel on the instrument. In addition, the relatively humidity of the atmosphere in the laboratory indicates a water concentration of $\sim 10^4$ ppm. The QCL tuning range was specifically chosen to avoid strong water absorption lines but there are a number of weaker absorption features that are accessible due to the high concentration of water.

FIGS. 14a and 14b show atmospheric absorption spectra in two spectral regions which includes atmospheric water, $CH_4$ and $N_2O$. The fitted concentrations were 3299 ppm ($H_2O$), 0.188 ppm ($N_2O$) and 1.44/1.47 ppm ($CH_4$). Minimum detectable concentrations were 1823 ppm.m ($H_2O$), 379 ppb.m ($N_2O$) and 2.5/1.1 ppm.m ($CH_4$). These numbers depends of the particular absorption cross-sections of the corresponding lines. The upper panels show the experimental spectra (points) and fitted spectra using the OEM algorithm (continuous line). The lower panels show the residual between the experimental and fitted spectra.

The person skilled in the art will appreciate that the arrangement set out above is exemplary, and the alternative design choices may be made without falling outside the scope of the invention as claimed.

The invention claimed is:

1. An active heterodyne detection system comprising a continuously tuneable laser source emitting infra-red radiation, a beamsplitter configured to split the infra-red radiation into a first part and a second part, a frequency shifting device configured to provide a frequency shift between the first part and the second part, beam direction optics configured to direct the first part of the infra-red radiation to a target, beam collection optics configured to collect a scattered component of the first part of the infra-red light from the target, wherein a local oscillator comprises the second part of the infra-red radiation and wherein the active heterodyne detection system further comprises a mixer and a detector, wherein the mixer is adapted to mix the scattered component and the local oscillator and to route the mixed scattered component and local oscillator to the detector and wherein the detector is adapted for heterodyne detection over a continuous spectral range.

2. A detection system as claimed in claim 1 wherein the continuously tuneable laser source is a quantum cascade laser.

3. A detection system as claimed in claim 2 further providing a temperature controller to tune the wavelength and stabilize the frequency of the infra-red light.

4. A detection system as claimed in claim 1, wherein the laser source is provided in an external cavity configuration with a diffraction grating for wavelength selection and tuning.

5. A detection system as claimed in claim 1, wherein the frequency shifting device is a acousto-optical modulator.

6. A detection system as claimed in claim 5, wherein a zeroth order mode of the acousto-optical modulator is used for monitoring of the laser source.

7. A detection system as claimed in claim 5, wherein the frequency shift is applied to the second part of the infra-red radiation and a first order mode of the acousto-optical modulator is used as the local oscillator.

8. A detection system as claimed in claim 5, wherein the frequency shift is applied to the first part of the infra-red radiation and a first order mode of the acousto-optical modulator is directed to the target.

9. A detection system as claimed in claim 5, wherein the detection system further comprises an attenuator between the laser source and the acousto-optical modulator, and wherein the attenuator is controlled by monitoring of power of the laser source.

10. A detection system as claimed in claim 9, wherein the attenuator is a polarizer.

11. A detection system as claimed in claim 1, wherein the laser source is mounted on a cold plate cooled by a Peltier cooler, and wherein the Peltier cooler is suspended from the cold plate.

12. A detection system as claimed in claim 11, wherein the Peltier cooler comprises a heat exchanger.

13. A detection system as claimed in claim 1, further comprising a mount for the laser source, wherein the mount comprises a support with high insulation and low thermal expansion.

14. A detection system as claimed in claim 13, wherein the support comprises one or more fiberglass clamps.

15. A detection system as claimed in claim 14, wherein a plurality of ceramic elements are provided on the one or more fiberglass clamps to support the mount at a plurality of point contacts.

16. A detection system as claimed in claim 1, wherein the beam direction optics, the beam collection optics and the mixer are all comprised in a reflective optical system.

17. A detection system as claimed in claim 16, wherein the reflective optical system comprises one or more beamsplitters.

18. A method of heterodyne detection comprising:
tuning a laser source to emit infra-red radiation to scan a continuous spectral range;
splitting the infra-red radiation into a first part and a second part;
providing a frequency shift between the first part and the second part;
directing the first part of the infra-red radiation to a target;
providing the second part of the infra-red radiation as a local oscillator;
collecting a scattered component of the first part of the infra-red light from the target;
mixing the scattered component and the local oscillator and routing them to a detector for heterodyne detection; and
processing a detected signal to provide output over a continuous spectral range.

19. A method as claimed in claim 18, wherein tuning the laser source comprises providing a sawtooth waveform to modulate an injection current of the laser source.

20. A method as claimed in claim 18, wherein the processing step comprises use of an optimum estimation method to provide output.

* * * * *